(12) United States Patent
Carroll et al.

(10) Patent No.: US 7,813,538 B2
(45) Date of Patent: Oct. 12, 2010

(54) SHADOWING PIPE MOSAICING ALGORITHMS WITH APPLICATION TO ESOPHAGEAL ENDOSCOPY

(75) Inventors: Robert E. Carroll, Seattle, WA (US); Eric J. Seibel, Seattle, WA (US); Steven M. Seitz, Seattle, WA (US)

(73) Assignee: University of Washington, Seattle, WA (US)

( * ) Notice: Subject to any disclaimer, the term of this patent is extended or adjusted under 35 U.S.C. 154(b) by 817 days.

(21) Appl. No.: 11/749,959

(22) Filed: May 17, 2007

(65) Prior Publication Data

US 2008/0262312 A1 Oct. 23, 2008

Related U.S. Application Data

(60) Provisional application No. 60/912,237, filed on Apr. 17, 2007.

(51) Int. Cl.
*G06K 9/00* (2006.01)
*A61B 5/05* (2006.01)

(52) U.S. Cl. .................. 382/128; 382/321; 600/425

(58) Field of Classification Search .............. 382/100, 382/128, 129, 130, 131, 132, 133, 134, 168, 382/181, 199, 203, 214, 232, 255–258, 274, 382/275, 276, 285, 305, 312, 321; 356/369; 600/425; 250/461.2

See application file for complete search history.

(56) References Cited

U.S. PATENT DOCUMENTS

| | | | | |
|---|---|---|---|---|
| 3,470,373 A | * | 9/1969 | Brewer et al. | 250/461.2 |
| 3,497,690 A | * | 2/1970 | Bahr et al. | 250/461.2 |
| 3,598,471 A | * | 8/1971 | Baldwin et al. | 359/562 |
| 3,657,537 A | * | 4/1972 | Wheeless et al. | 250/461.2 |
| 4,695,163 A | * | 9/1987 | Schachar | 356/369 |
| 7,738,945 B2 | * | 6/2010 | Fauver et al. | 600/425 |

FOREIGN PATENT DOCUMENTS

| | | |
|---|---|---|
| EP | 0 713 672 | 5/1996 |
| EP | 0 520 388 | 9/1996 |
| EP | 0 712 032 | 12/2001 |
| WO | WO 01/97902 | 12/2001 |
| WO | WO 01/97902 A2 * | 12/2001 |

* cited by examiner

*Primary Examiner*—Seyed Azarian
(74) *Attorney, Agent, or Firm*—Ronald M. Anderson

(57) ABSTRACT

In connection with imaging an inner surface of a body lumen, a mosaiced image is created from discrete images or a video produced with a small camera, as the camera is moved through the lumen. In one embodiment, a tethered capsule with a scanning optical fiber provides the images, although other types of endoscopic cameras can instead be used. A surface model of the lumen and camera pose estimates for each image or frame are required for this task. Camera pose parameters, which define camera alignment, are determined for six degrees-of-freedom. The size of each frame projected as a strip on the surface model depends on the longitudinal movement of the camera. The projected frames are concatenated, and the cylinder is unrolled to produce the mosaic image. Further processing, such as applying surface domain blending, improves the quality of the mosaic image.

27 Claims, 13 Drawing Sheets

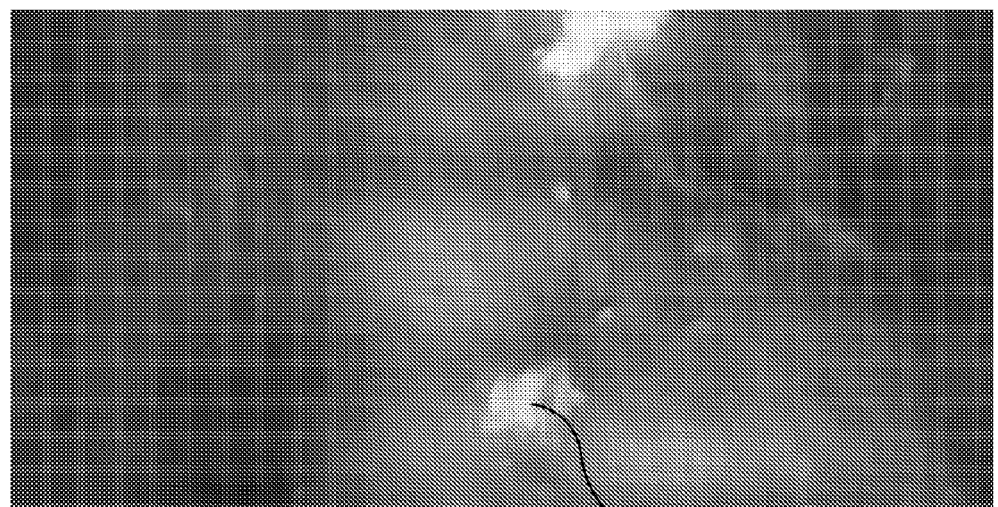
*FIG. 8A*
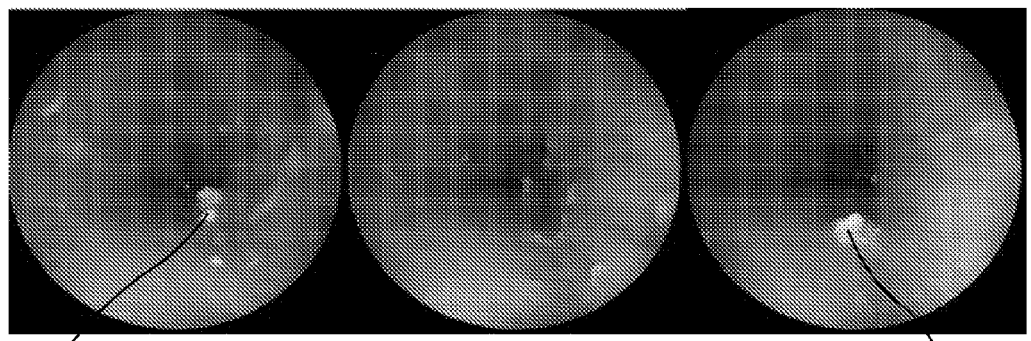
*FIG. 8B*
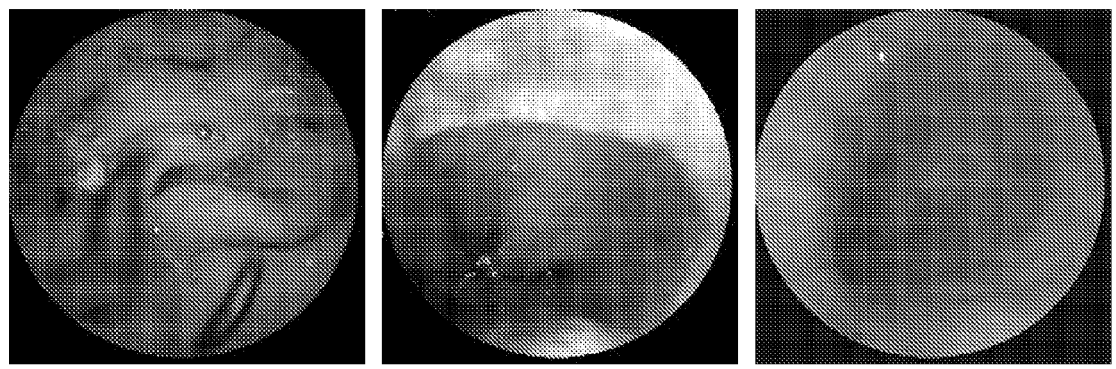
*FIG. 9A*     *FIG. 9B*     *FIG. 9C*

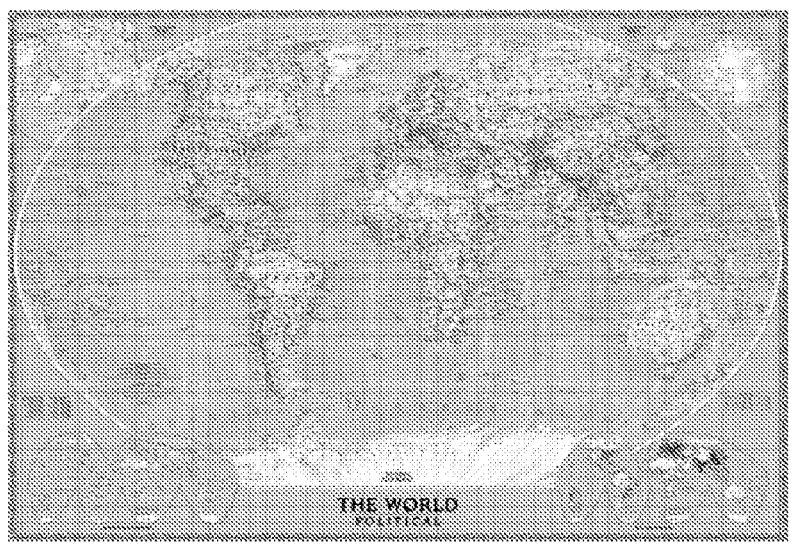
FIG. 12A
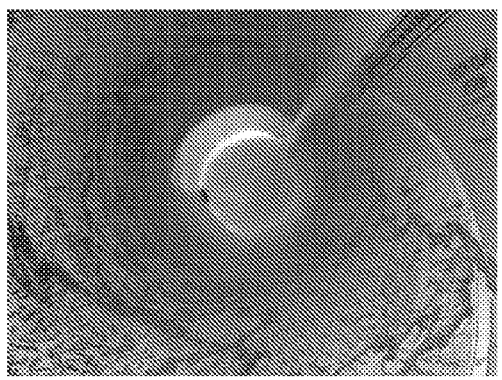   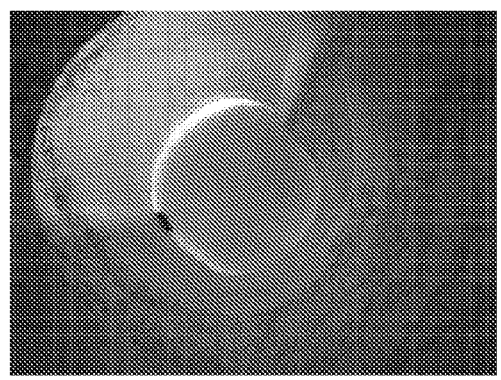
FIG. 12B          FIG. 12C
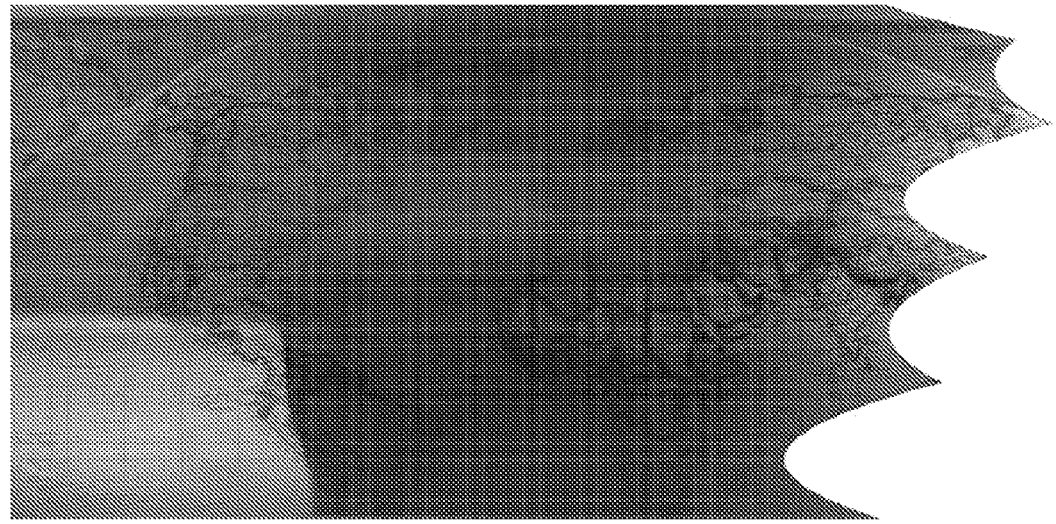
FIG. 12D

BANDED HESSIAN MATRIX USED IN GLOBAL OPTIMIZATION IS CONSTRUCTED FROM HESSIANS OF THE PAIRWISE REGISTRATION, WHERE OVERLAPPING REGIONS ARE SUMMED

SHADOWING PIPE MOSAICING ALGORITHMS WITH APPLICATION TO ESOPHAGEAL ENDOSCOPY

RELATED APPLICATIONS

This application is based on a prior copending provisional application Ser. No. 60/912,237, filed on Apr. 17, 2007, the benefit of the filing date of which is hereby claimed under 35 U.S.C. §119(e).

GOVERNMENT RIGHTS

This invention was made with U.S. Government support under grant No. IIS-0413148 awarded by the National Science Foundation (NSF). The U.S. Government has certain rights in the invention.

BACKGROUND

The incidence of esophageal adenocarcinoma is rising faster than for any cancer in the U.S, and is the sixth leading cause of death from cancer in men. Esophageal adenocarcinoma is believed to arise from a condition known as Barrett's esophagus (BE) in which the esophageal epithelium is marked by abnormal intestinal-type cell growth, also believed to result from chronic gastroesophageal reflux disease (GERD). Although it is unknown whether BE is a necessary precursor to all cases of esophageal cancer, it is a well documented and clearly recognized risk factor for esophageal adenocarcinoma. As will be evident in the exemplary image shown in FIG. 1, BE mucosa tissue 10 appears salmon pink in color, in contrast to the normal pearly white squamous mucosa 12 of an esophagus 14 (these tissue types are shown by gray scale, which only indicates color). Although screening for esophageal cancer is not deemed appropriate for the general population, periodic examination of patients with BE is recommended in order to identify dysplasia or cancer at an earlier and more treatable stage. While standard endoscopy and tissue biopsy are sufficient for the monitoring of patients diagnosed with BE, 95% of esophageal adenocarcinoma develops in patients with previously undiagnosed BE, proving that current endoscopic screening efforts are inadequate.

When considering a screening strategy for a condition such as BE, it is important to consider several factors: disease progression, availability of screening resources, performance of a particular screening test (sensitivity and specificity), accessibility to treatment, the willingness of patients to undergo screening, and the associated cost. BE is a fairly common condition among patients having the symptom of heartburn, with an estimated prevalence ranging from 6%-12%. Currently, screening is performed using a standard gastrointestinal (GI) endoscope on a sedated patient to examine and biopsy any abnormal appearing mucosa. An assessment of the presence of BE by an endoscopist has been shown to have a relatively high sensitivity and specificity when compared to pathologic confirmation. The additional use of topically-applied dyes for chromoendoscopy, expanded magnification, and separate analysis from narrow-band excitation may improve the sensitivity and specificity for BE, though their clinical utility is currently unproven. Once diagnosed, BE is treated by reducing the symptoms of GERD using pharmaceuticals and/or surgery with new highly successful therapies being developed specifically for BE. While there are no randomized studies demonstrating that screening and surveillance improve BE patient outcomes, retrospective cohort studies suggest that BE patients undergoing surveillance have significantly improved survival compared to controls.

In a physician survey, 62% indicated that if unsedated endoscopy were made available to primary care physicians in an office setting, an increase in BE screening would result. Unsedated endoscopy using a thinner endoscope is an alternative to standard endoscopy, but is not commonly used in the USA, possibly due to patient lack of acceptance of the common transnasal approach. Finally, there is ongoing research aimed at finding biomarkers that identify esophageal adenocarcinoma in its pre-cancerous and neoplastic stages, since it is believed that genetic changes precede any morphological changes found during histological analysis. However, at present, there is no single biomarker available for which a negative indicator test result would warrant discontinued screening of a patient.

Ideally, a new screening test for BE should be as sensitive and specific as standard endoscopy, but should not require sedation and should have low risk and low cost. The current cost for standard endoscopy that has been indicated by the Center for Medicaid and Medicare Services (CMMS) is several hundred dollars, excluding biopsies. The CMMS cost for esophageal capsule endoscopy is even higher. Nevertheless, screening and monitoring with standard endoscopy followed by esophagectomy for surgical candidates with high-grade dysplasia or cancer, or endoscopic therapy for cancer patients who were not operative candidates has been reported to be cost-effective.

Wireless capsule endoscopy or "pill" endoscopy is a recent alternative to standard endoscopy, which uses a modified capsule containing two cameras, a battery source, and a wireless transmitter for sending images to an external digital recorder. However, untethered capsule endoscopy is limited because it yields random views of the esophagus, produces images at sub-video frame rates (~2 per sec), and increases the overall cost of diagnosis. It would be preferable to employ a tethered capsule to achieve direct control over a camera view by an endoscopist, enable imaging at near video frame rates, and reduce overall cost. Furthermore, there is a need to provide images in a mosaic format, in which the inner surface of the esophagus (or other body lumens to which the technique is applied) can be viewed as an unrolled, flat image over an extended longitudinal depth.

Accordingly, it would be beneficial to employ a new low-cost device specifically for BE screening and for imaging inside the esophagus and other types of body lumens that is based on a completely new type of endoscope imaging technology. Instead of using passive illumination and a CCD array for image capture, it would be desirable to employ a single optical fiber to scan a surface using laser illumination, while responding to backscattered light, which is recorded one pixel at a time to form an image. The fiber scanner and lenses used for imaging should be housed within a capsule that is coupled to a tether comprising a single optical fiber employed for illumination, as well as scanner drive lines, and a plurality of return plastic optical fibers. In a manner similar to standard endoscopy, a base station can be provided that contains light sources as well as optical detectors and software needed to provide a machine vision software tool for clinicians. In order to judge short (<3 cm) versus long segment BE, it should be possible for clinicians to measure the extent of suspected BE above the top of the gastric folds.

In addition, if conventional imaging devices are used instead of the new type of imaging device noted above, software running on a system coupled to the imaging device should still enable a mosaic of the entire esophagus inner surface (or the inner surface of other types of body lumens) to be automatically generated from the images provided by the device to aid a clinician in visualizing the extent of BE and identify likely sites for future biopsies. A virtual colonoscopy using computed tomography and a new mosaic panorama perspective should enable a radiologist to read a patient's data significantly faster than relying upon a conventional virtual colonoscopy perspective, without detriment to detection rate. The laser-scanning imaging provided by an imaging probe and the application of integrated mosaicing software should thus be useful for screening and surveillance of neoplasia and other diseased tissues within a lumen more efficiently and at lower cost than can be achieved with conventional techniques.

SUMMARY

Thus, one of the motivating factors in developing the novel technology described below was to create a screening procedure for Barrett's esophagus that can potentially identify at-risk patients so they can be monitored and treated before cancer develops. However, this technology also has application to imaging body lumens other than the esophagus and for other purposes than identifying Barrett's esophagus condition in a patient. Moreover, it is contemplated that mosaic images can be produced with other types of imaging devices or cameras besides the novel imaging device that uses an optical fiber scanner that is described below. The imaging of body lumens to produce mosaic images of their inner surface is thus not intended to be limited to the use of this novel imaging device, but can also be done with almost any type of imaging device.

In connection with its use for detecting Barrett's esophagus, the screening procedure starts with a patient swallowing a camera, which in the initial exemplary embodiment is in the form of a tethered pill-sized capsule. The technician then either manually or mechanically extracts the camera from the esophagus of the patient. While the camera is being withdrawn, a video of the patient's esophagus (or other body lumen) is captured. The camera is oriented to look down the central axis of the esophagus, so the view that is captured while the camera is being withdrawn is analogous to that observed while driving a vehicle backward out of a tunnel. By processing this captured video signal produced by the camera, software running on a computing device, such as a personal computer, creates a mosaic image of the esophagus that is "unzipped." This mosaic image comprises small strips taken from individual video frames that are stitched together in a way corresponding to the extent of motion in the scene that was captured. The result is a single image that shows the patients' entire inner esophageal surface.

In order to create a representation of the esophageal surface using an endoscopy video sequence, two basic elements are required, i.e., a surface model of the esophagus, and a camera pose estimation for each video frame. With this knowledge, each frame can be projected back onto the model to texture-map its surface. The texture-mapped model must then be transformed into a flat image that comprises a mosaic image of the inner surface of the esophagus or other type of body lumen. The surface is modeled as a cylinder, because the esophagus is generally cylindrical in shape and because a cylinder can be easily displayed as a two-dimensional image when "unrolled" to provide the mosaic image. It should be understood that in connection with the following disclosure, the terms "lumen," "body lumen," "cylinder," "pipe," and "tube" should all be viewed as generally referring to the generally cylindrical surface that is being imaged with a camera to form the mosaic image.

To estimate camera motion, a warping function is defined based on camera pose (position and orientation) and is minimized across all consecutive frame pairs. The result is a pose estimate for each frame that can be used to project the frame onto the surface of the model. To compensate for illumination changes in the scene, the exemplary procedure first performs a neighborhood-normalization of each frame before the alignment is done. From each projected frame is taken a ring having a width corresponding to the extent of forward motion. The rings are concatenated together to produce the texture-mapped cylinder, which can then be unwrapped to provide the mosaic image. As a final step to compensate for any seaming artifacts, gradient domain blending can be applied to the mosaic image.

An exemplary embodiment of the present approach includes an alignment technique to solve for the entire six degrees-of-freedom camera pose for each image frame. From a single image frame with a known pose, the image can be warped to create virtual views from other locations, and this step produces a "pipe warp." This transformation is used to construct an energy function based on the camera pose parameters. Minimizing this energy function provides the camera pose estimations for each frame. Using this general exemplary framework, it is possible to extend the surface model for more accurate results.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 6A:
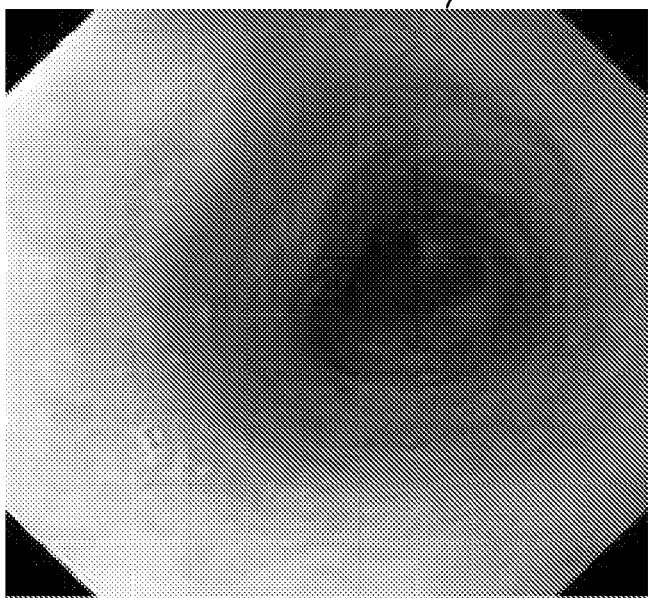
Figure 6B:
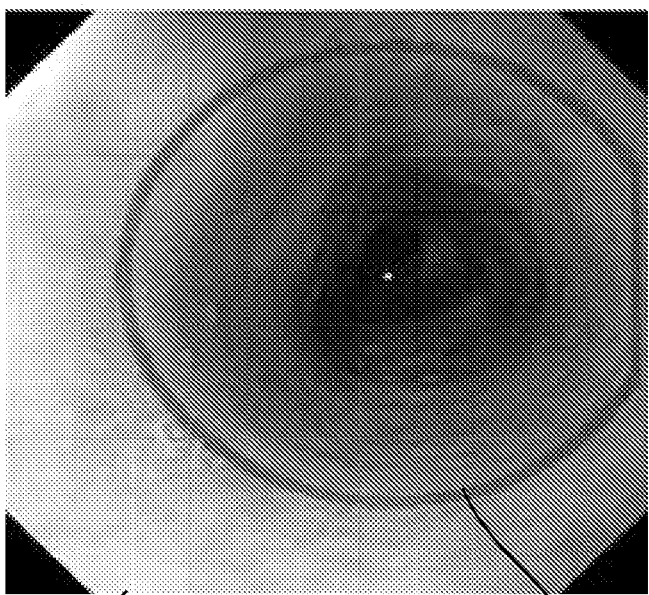
Figure 6C:
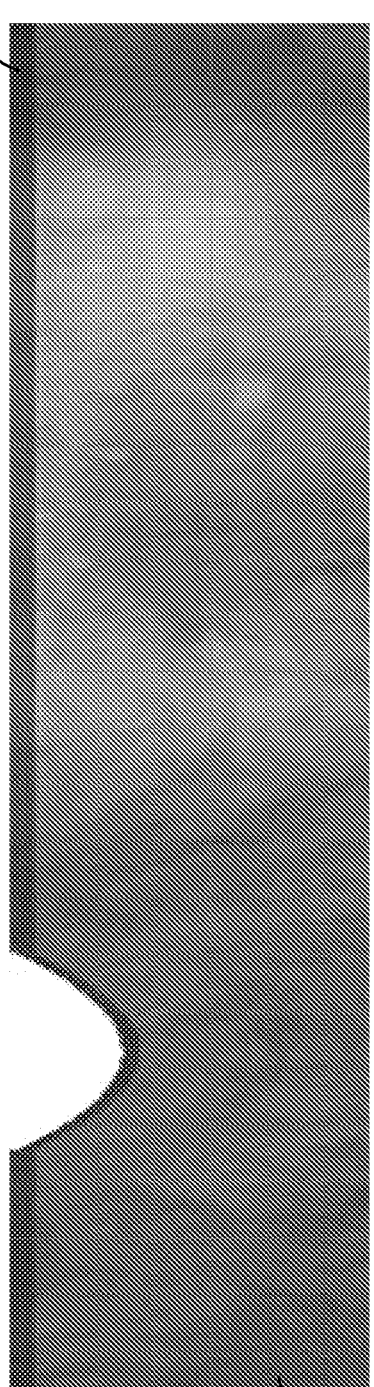
Figure 7A:
Figure 7B:
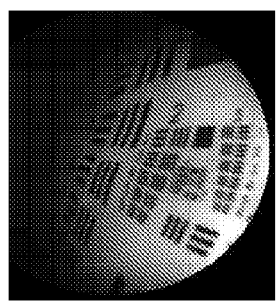
Figure 7C:
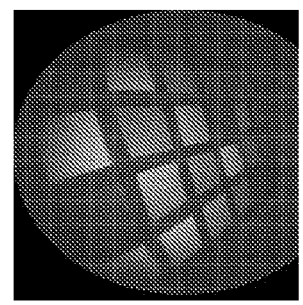
Figure 7D:
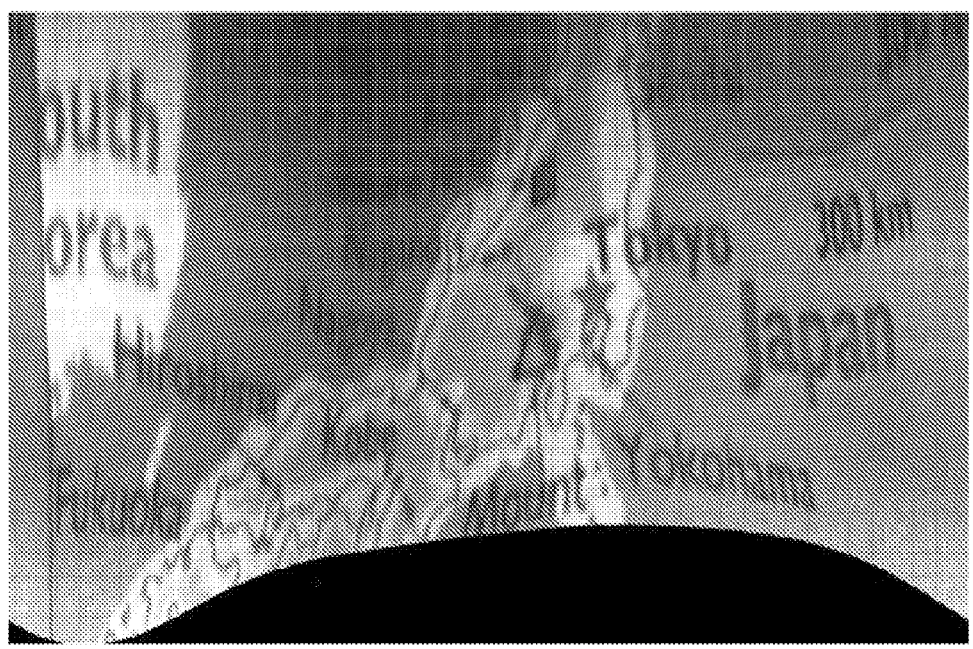
Figure 10A:
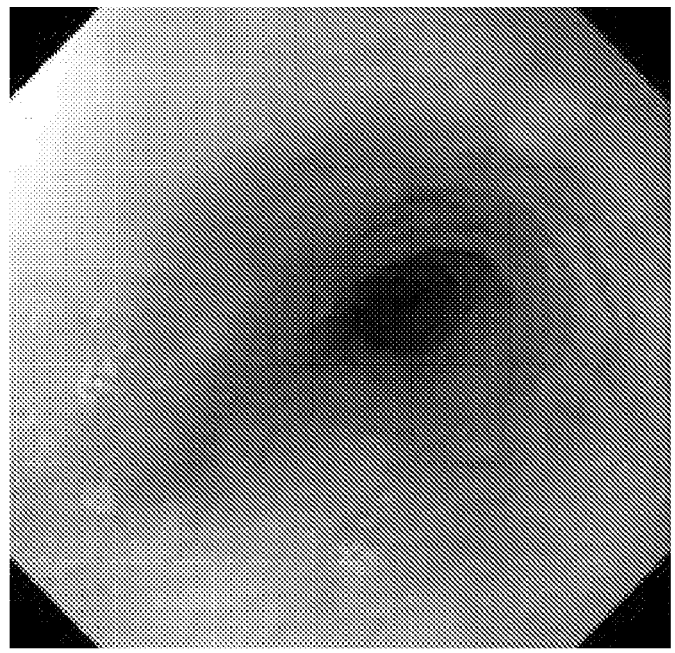
Figure 10B:
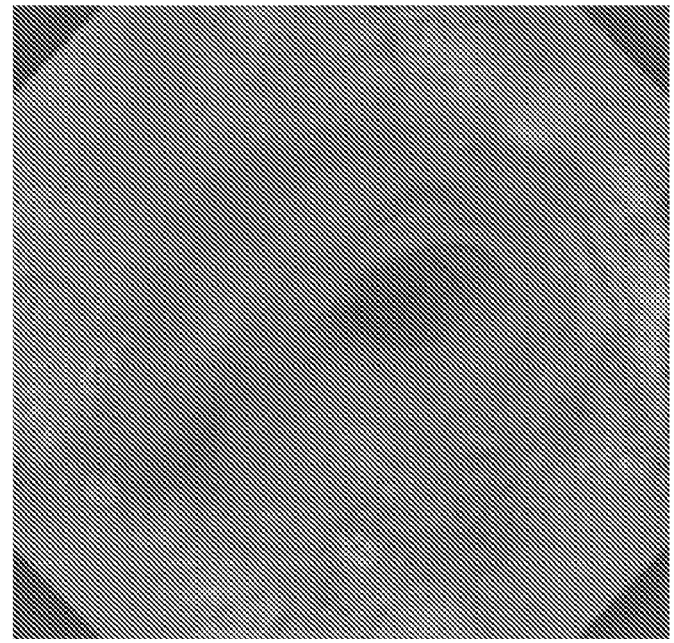
Figure 11A:
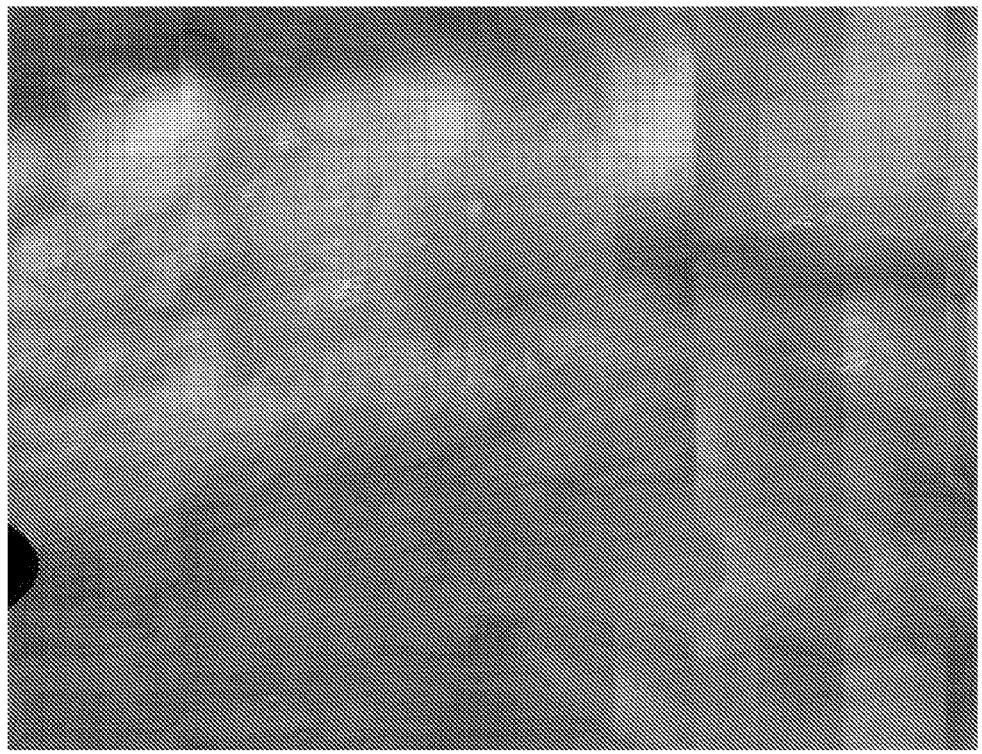
Figure 11B:
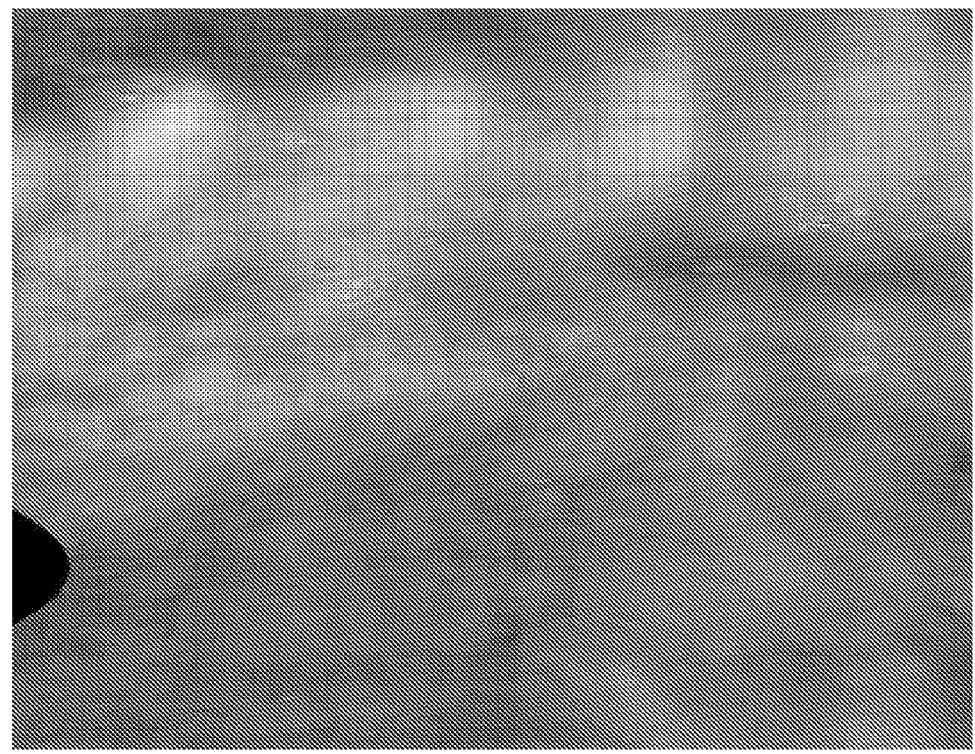
Figure 13A:
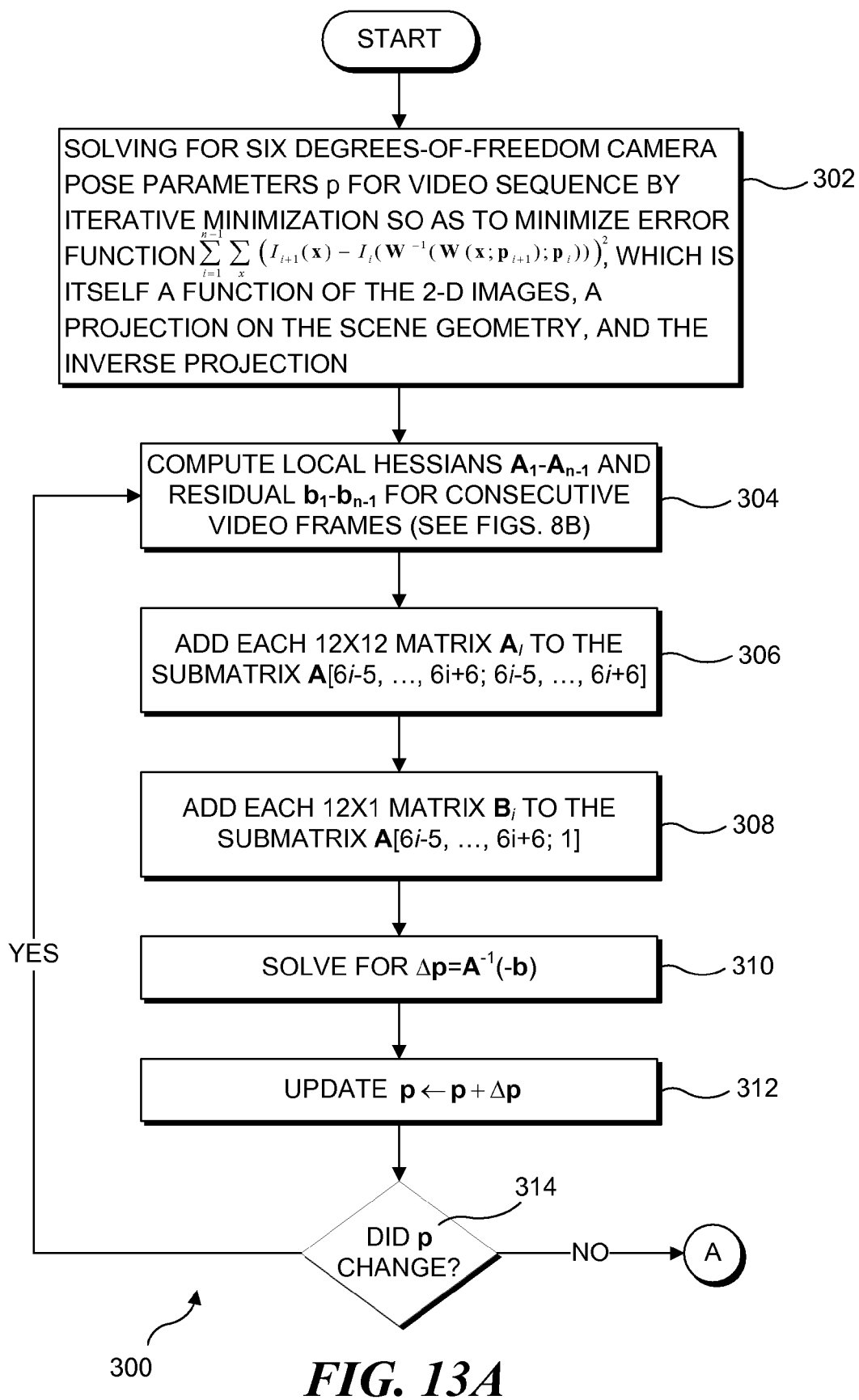
Figure 13B:
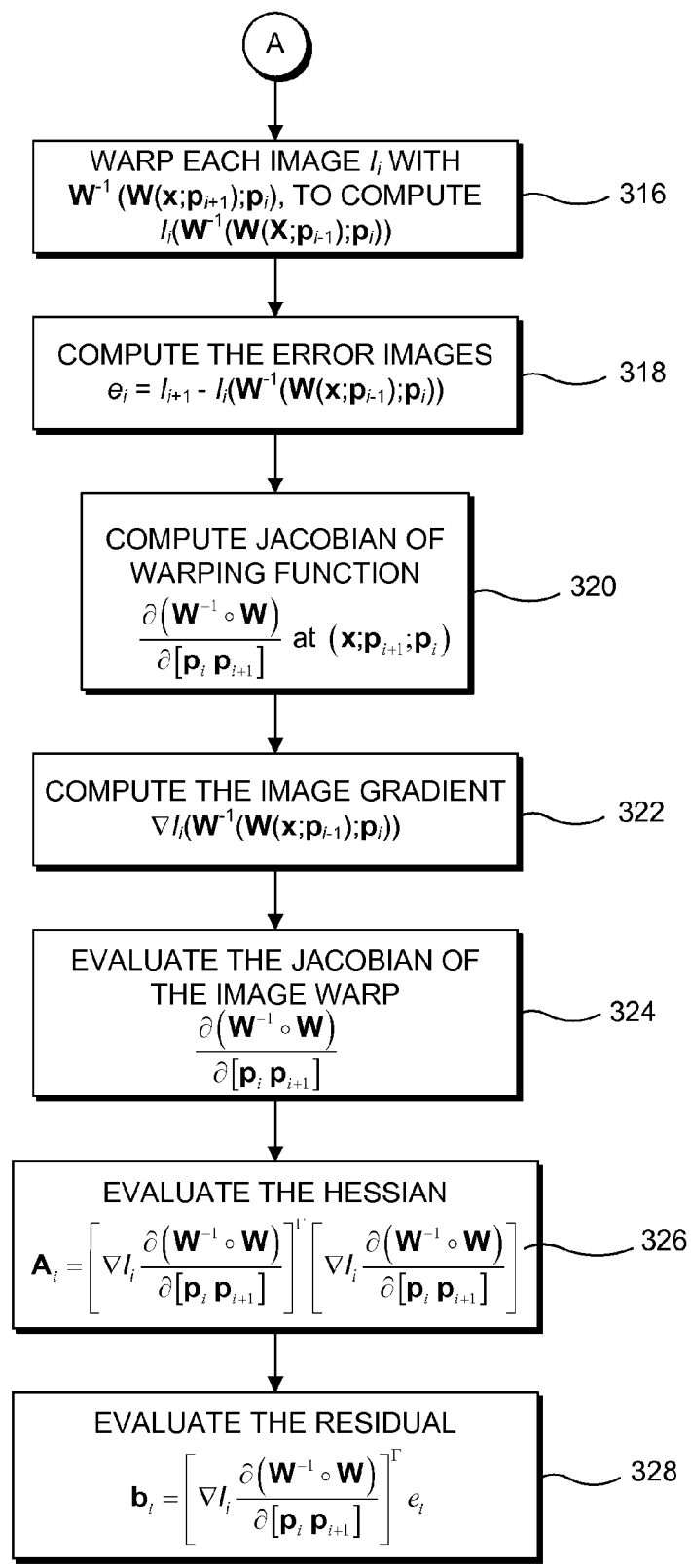
Figure 13C:
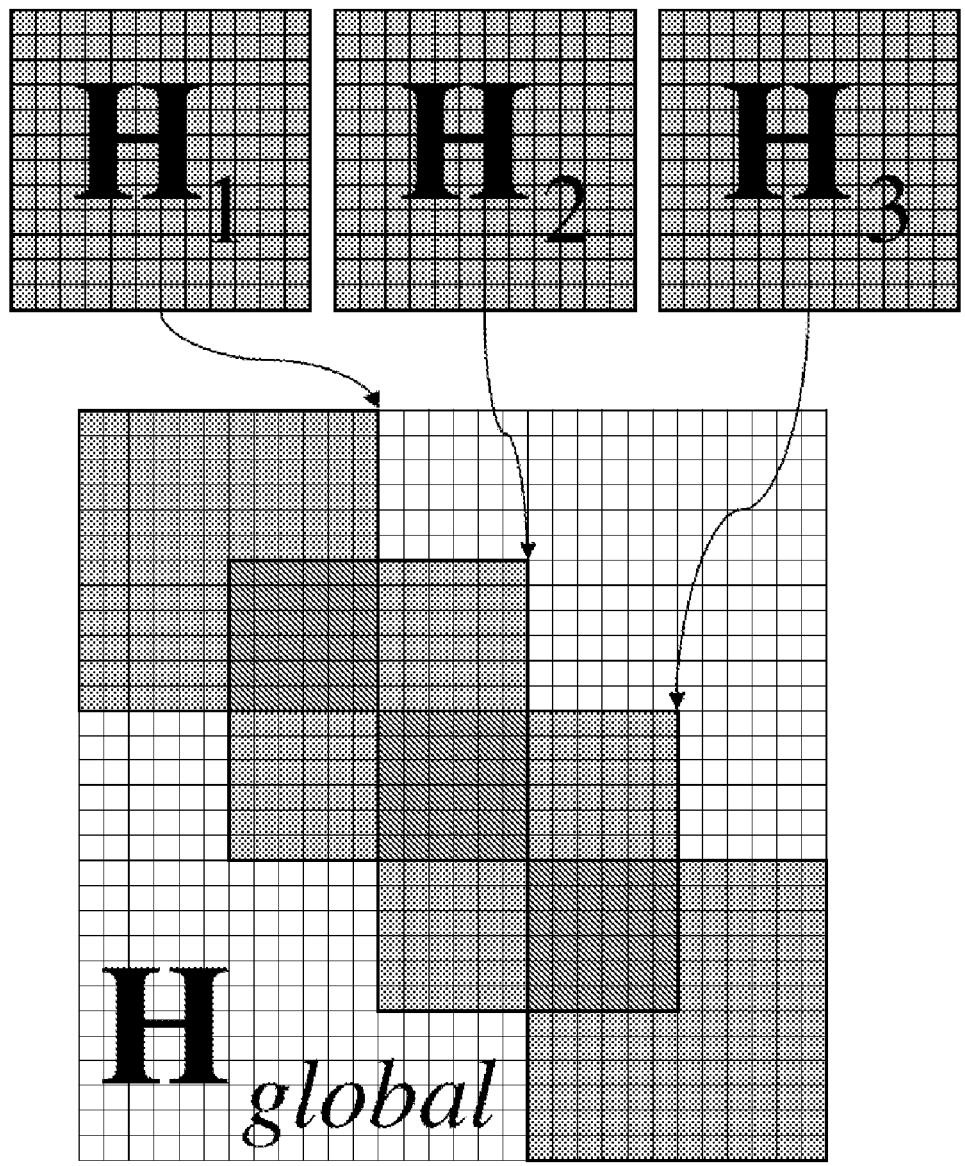
Figure 14:
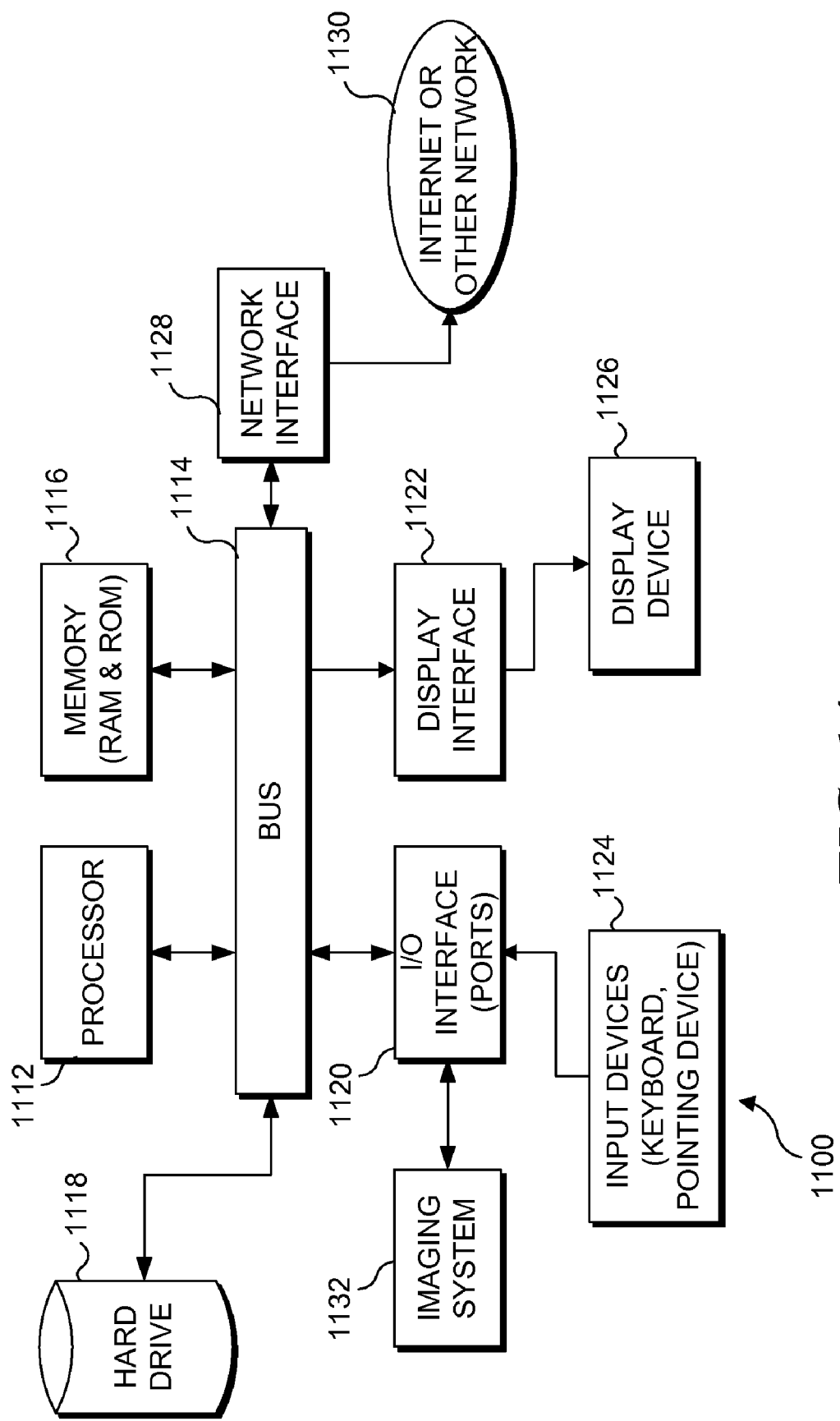

FIGS. 6A, 6B, and 6C respectively illustrate an exemplary image of an esophagus, the image of the esophagus with a dark line to show the location of the strip that is projected to produce the mosaiced image, and the resulting strip (the notch is caused by the strip being limited by the edge of the original image);

FIG. 7A is a photo showing an exemplary TCE system;

FIGS. 7B and 7C are respectively images of an Edmund Optics USAF 1951 test target, and a Gretag Macbeth Mini Color Chart made using the TCE;

FIG. 7D is a mosaic image made by imaging inside a 1-inch tube of rolled paper on which a map is printed, through which the TCE was pulled slowly (~2 mm/sec) and kept roughly centered on its central axis, illustrating that the mosaic images are generated by the TCE system with noticeable but acceptable levels of distortion for the purpose of identifying and mapping regions of color variation;

FIG. 8A is an exemplary mosaic image of the upper esophagus of a pig produced using the novel approach disclosed herein;

FIG. 8B illustrates three images that show bile coated particles of food in the esophagus of the pig, as referenced in FIG. 8A;

FIGS. 9A, 9B, and 9C respectively illustrate exemplary images of a human esophagus, which were produced by the TCE system and show gastric folds (FIG. A), the important squamo-columnar junction where the stomach mucosa (red in color, but darker portion in the gray scale image) transitions to the esophageal mucosa (light pink in color or very light portion in gray scale), and another portion of the esophagus above this transition point;

FIGS. 10A and 10B respectively illustrate images made with the TCE that show an original (FIG. 10A), and a neighborhood-normalized frame (FIG. 10B) produced from endoscopy video output from the TCE, where neighborhood normalization compensates for illumination differences between frames;

FIGS. 11A and 11B respectively illustrate an exemplary esophagus mosaic image without gradient domain blending, and the corresponding esophagus mosaic image with gradient domain blending;

FIG. 12A illustrates a world map as it appears on a flat sheet of paper, before being formed into a cylindrical tube that was then used to produce a video of the inner surface of the tube so that the video images could be processed by the present technique to form a mosaic image of the surface;

FIGS. 12B and 12C respectively illustrate two exemplary input video frames of the inner surface of the world map of FIG. 12A after it was formed into a cylindrical tube;

FIG. 12D illustrates the mosaic image produced using the present technique from the video of the world map (FIG. 12A) that was formed into a tube, with input video frame images like those shown in FIGS. 12B and 12C, where mixed lighting exposures evident in the mosaic image are caused by uneven lighting conditions within the tube;

FIGS. 13A and 13B together comprise a flowchart that illustrates exemplary logical steps for producing a mosaic image from a video of a generally cylindrical surface, in accord with the present approach;

FIG. 13C is a schematic illustration illustrating how a banded Hessian matrix used in global optimization is constructed; and FIG. 14 is a schematic block diagram of a generally conventional personal computer (PC), which is suitable for carrying out the processing steps used to produce the mosaic image of the inner surface of a body lumen as described herein.

DESCRIPTION

Figures and Disclosed Embodiments are not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Exemplary Embodiment of TCE

Figure 1:
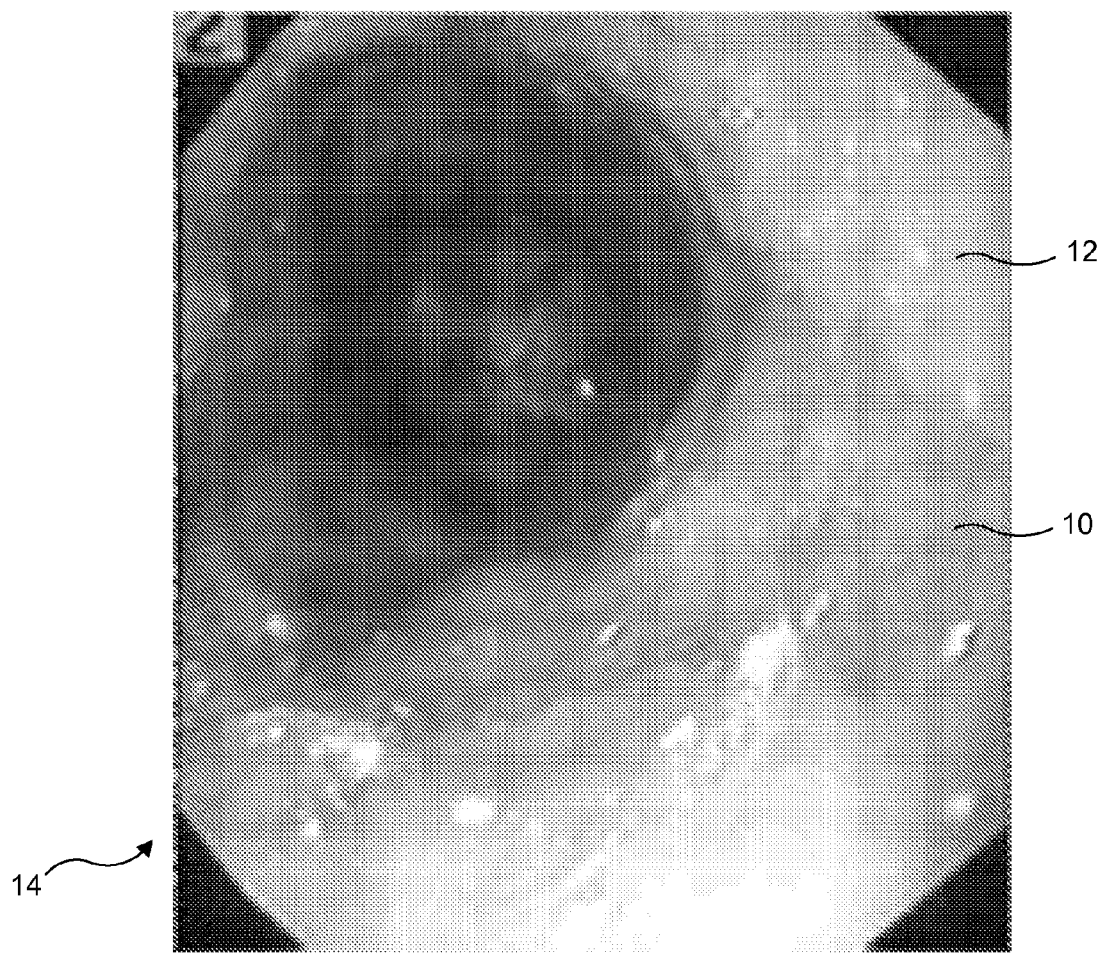
FIG. 1 is an exemplary image of an esophagus taken with a camera comprising an exemplary scanning fiber endoscope capsule, as described below.
Figure 2A:
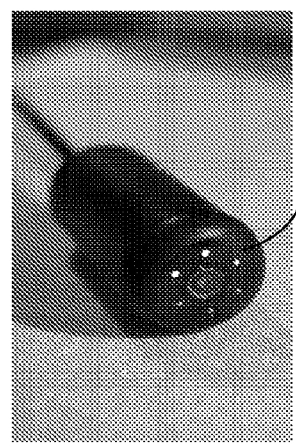
FIG. 2A is a photograph of the exemplary tethered capsule endoscope (TCE) using a scanning fiber camera, which in one exemplary application, is configured to be swallowed by a patient to image the inner surface of the patient's esophagus.
Figure 2B:
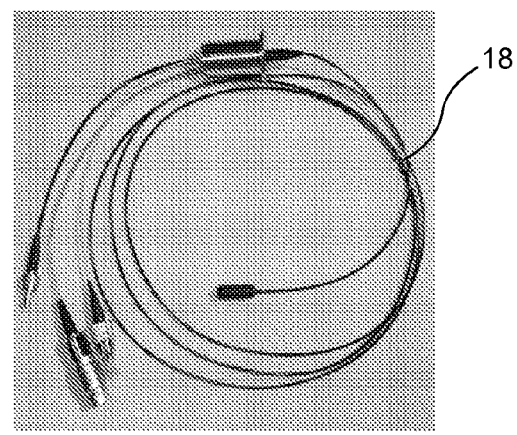
FIG. 2B is a photograph illustrating the components of the tether used for the TCE of FIG. 2A, which include a single optical fiber that is used for illumination, scanner drive lines, and six plastic optical fibers that convey light received from the tissue in a body lumen.
Figure 2C:
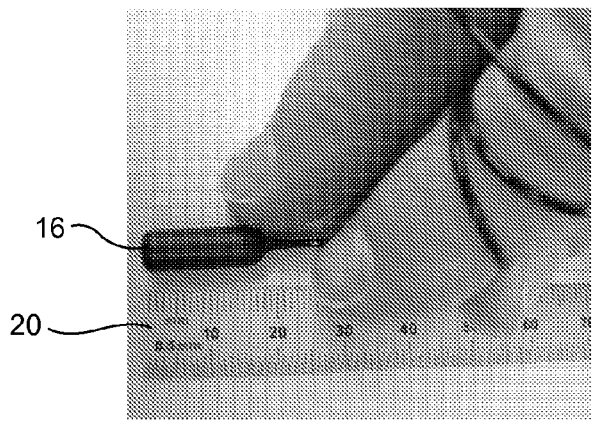
FIG. 2C is a photograph illustrating the relative length (and size) of the exemplary TCE, in connection with a metric ruler on which the device is positioned.

An exemplary embodiment of a TCE has been developed that comprises a scanning fiber endoscope (SFE), which was developed at the University of Washington. Like the SFE, the TCE uses a singlemode fiber scanner that is driven to move in a desired scanning pattern to scan a laser spot over tissue. In this embodiment, multimode optical fibers are employed to capture and record backscatter light signals received from the tissue, so that an image can be formed of the site as the light for each pixel is received by the multimode optical fibers. FIG. 2A illustrates an exemplary TCE 16 using a scanning optical fiber as a camera; FIG. 2B illustrates the components of a tether 18 used for the TCE of FIG. 2A, which includes a single optical fiber that is used for illumination, scanner drive lines, and six return plastic optical fibers (not separately identified in this Figure). FIG. 2C illustrates the relative length or size of exemplary TCE 16, in connection with a metric ruler 20 on which it is positioned.

Although much of the following discussion is directed to imaging the internal surface of a patient's esophagus, it must be emphasized that the TCE and the mosaicing algorithm described below are not limited only to the esophagus, but instead, can be used for imaging any generally cylindrical body lumen, e.g., the colon.

Figure 3:
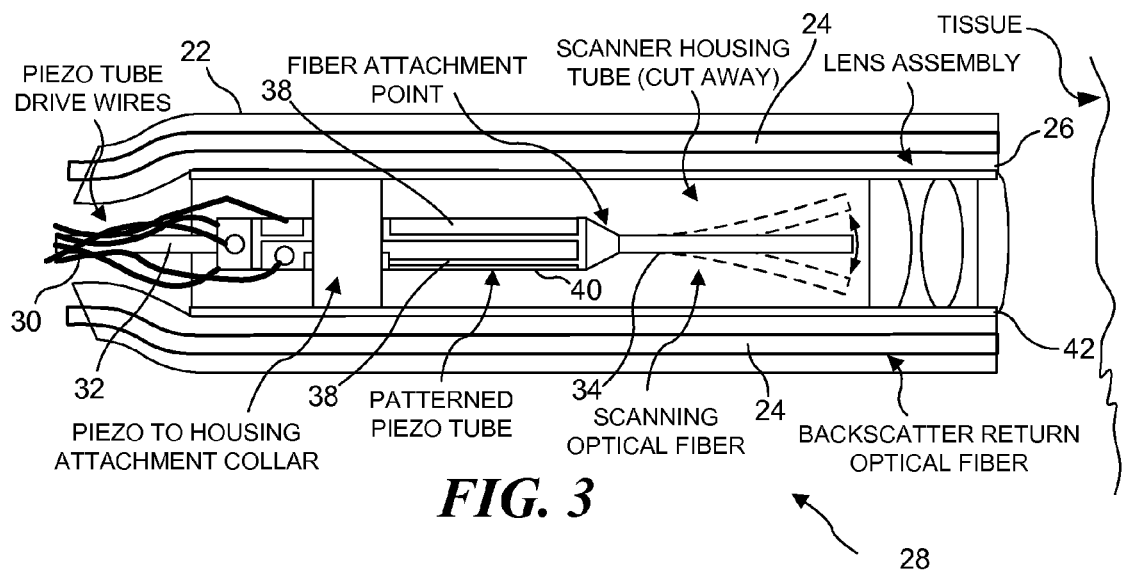
FIG. 3 is a cut-away schematic view of the exemplary TCE showing a scanning optical fiber and other components included therein.
Figure 5:
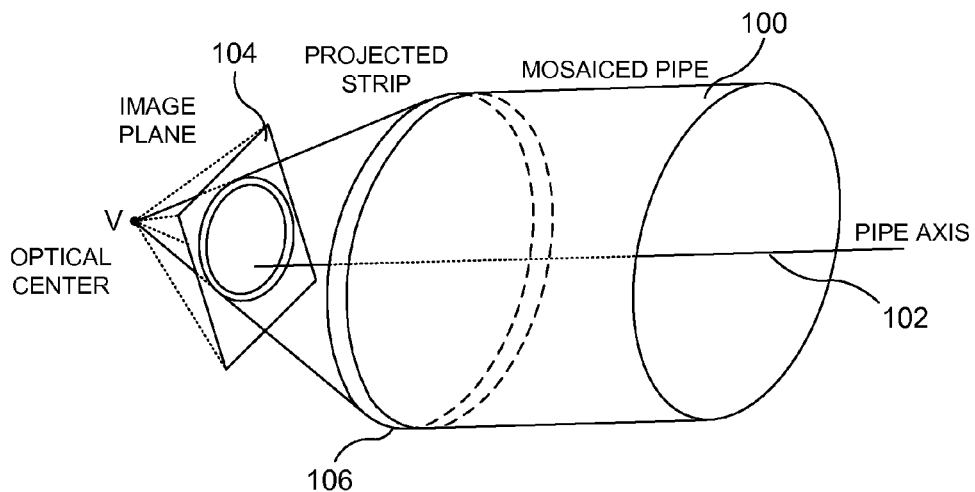
FIG. 5 is a schematic diagram graphically illustrating the exemplary approach used to project a strip from the image plane onto a mosaiced pipe or cylinder, using the present technology.

In this exemplary embodiment, the optical fiber scanner is driven to scan using a 420 micron diameter piezoelectric tube to which a 4.3 mm cantilevered length of singlemode optical fiber (Nufern 460-HP™) is affixed (see FIG. 3). The piezoelectric tube is plated with quadrant electrodes and energized with drive signals supplied through five 50 gauge wires that extend proximally through the tether. The piezoelectric tube, singlemode optical fiber, and an appropriate lens system are contained in a stainless steel tube having a 1.1 mm outer diameter and 13 mm length.

A package for TCE 16 was created by encapsulating the optical fiber scanner in a smooth medical grade plastic capsule housing 22 to aid in swallowing the device. The capsule housing dimensions (6.35 mm×18 mm) are those of a standard No. 2 capsule (available from Torpac Inc., Fairfield, N.J.) and were chosen over larger and smaller sizes for ease of swallowing and ability to handle, although this size should not be considered limiting, since larger or smaller capsules can instead be used, as desired. Six 250 micron diameter multimode optical fibers 24 (only two shown) are directed to a face 26 of the capsule to collect the backscattered light signal from tissue, for example, tissue comprising an internal wall of an esophagus. (In an alternative exemplary embodiment, one or more optical detectors could be included in the TCE instead of the plurality of multimode optical fibers, and the signals produced by the one or more optical detectors in response to the backscattered light can be conveyed proximally through conductive leads and used for producing an image of the site.) Wires 30 and optical fibers 24 and an optical fiber 32 that conveys the illumination light to a scanning optical fiber 34 are routed back from the capsule to the base station through thin flexible tether 18 (shown in FIG. 2B) that is about 1.4 mm in diameter in this exemplary embodiment. Wires 30 are used to apply drive signals to electrical quadrants 38 formed on a patterned piezo tube 40, which when excited by the electrical drive signal, drives scanning optical fiber 34 to move in a desired pattern (i.e., to vibrate at about its resonant frequency) relative to two generally orthogonal axes. Light emitted from the distal end of the moving scanning optical fiber passes through a lens assembly 42 and is focused on the tissue. The exemplary TCE used for testing was designed to meet the specifications shown below in Table 1.

Figure 4:
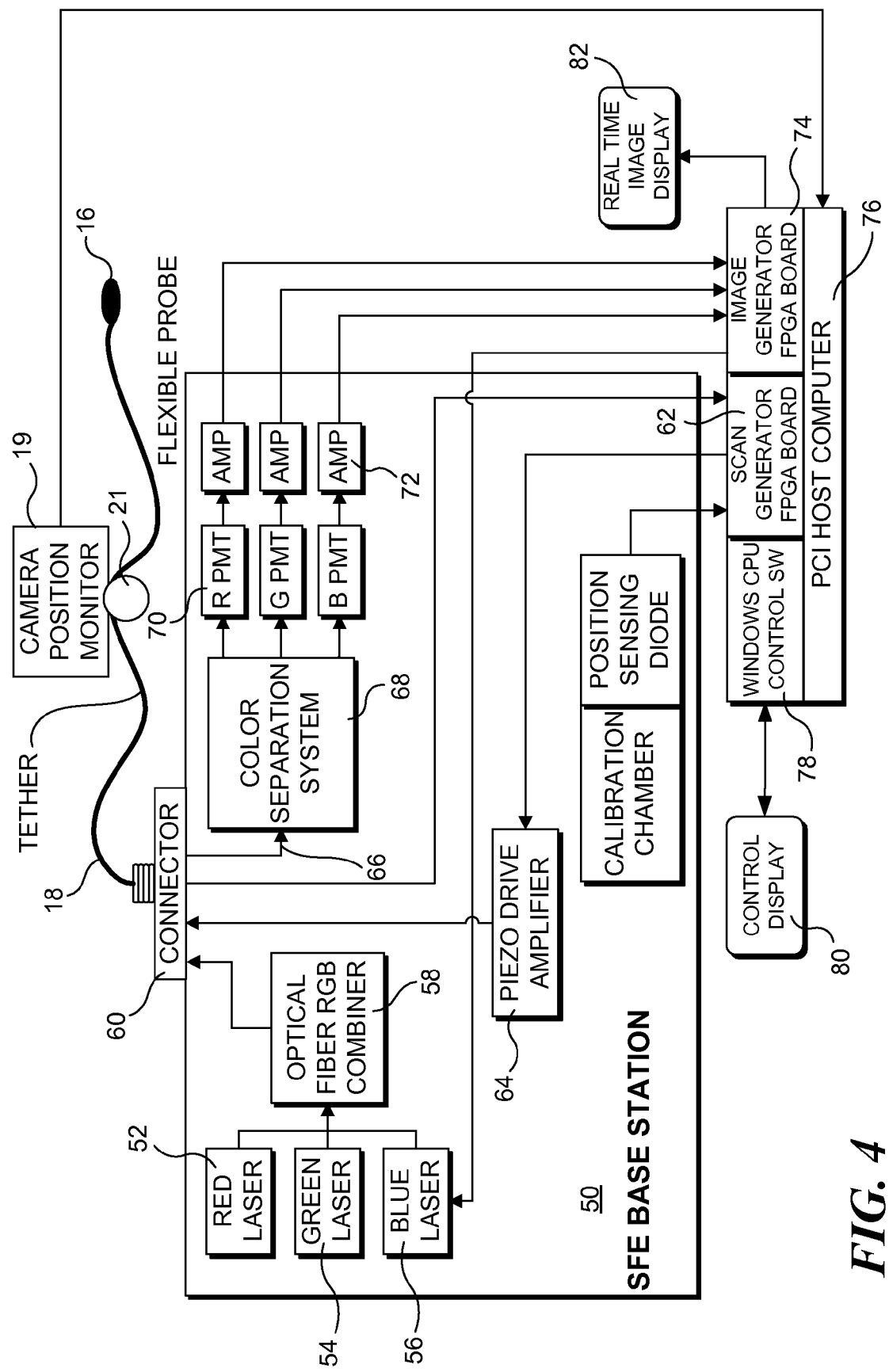
FIG. 4 is a functional block diagram of an exemplary system that is used for creating mosaic images of a patient's inner esophageal surface.

FIG. 4 illustrates the components of a base station 50, which includes a red (R) laser 52 that produces light having a wavelength of about 635 nm (e.g., a FiberMax™, available from Blue Sky Research), a green (G) laser 54 that produces light at a wavelength of about 532 nm (e.g., a Chromalase™, available from Blue Sky Research), and a blue (B) laser 56 that produces light having a wavelength of about 444 nm (available from Nichia Laser Diode and OZ Optics). Together, these three laser sources provide RGB laser light to an optical fiber combiner 58 (e.g., an RGB Combiner 40W004-001™ available from SIFAM). Optical fiber combiner 58 combines the RGB light from these lasers and supplies the combined laser light to a connector 60, which is coupled to tether 18. A camera position monitor 19 monitors the position of TCE 16 by tracking the movement of tether 18 as it is drawn over and thereby rotates a wheel 21 while the TCE is being pulled through a body lumen (not shown in this Figure) by the tether. However, alternative techniques for monitoring the position of the TCE within a body lumen are contemplated. A scan generator signal source (in this exemplary embodiment, a field programmable gate array (FPGA)) board 62 generates drive signals that are applied to a piezo drive amplifier 64. The amplified drive signals are supplied to connector 60 and are used to energize piezo electric tube driver 40 in the TCE. The base station also includes an optical fiber 66 that is coupled to a color separation system 68 (e.g., using dichroic beamsplitters). The color separation system separates the return light from the tissue in a patient's body lumen into separate RGB light bands and supplies these different color light signals to corresponding R, G, & B photomultiplier tube (PMT) optical detectors 70. The PMT optical detectors thus detect the three primary colors of return light conveyed through the multimode optical fibers, and the output signals from the PMT optical detectors are amplified by amplifiers 72, producing amplified signals that are input to an image generation board (i.e., in this embodiment, another FPGA board) 74.

The scan generator board and the image generator board are coupled to a PCI bus 76 of a host computer (not fully indicated in this Figure), which in this exemplary embodiment, includes a Windows™ software compatible central processor unit (CPU) 78 that is coupled to a control display 80. A signal produced by cameral position monitor 19 is supplied to CPU 78, to enable the CPU to scale the mosaiced imaged relative to the body lumen through the TCE is moved. The scaling of the mosaiced image relative to the position of the TCE in the body lumen enables a medical practitioner to diagnose a medical condition of tissue inside the body lumen based upon the mosaiced image, at specific points along the longitudinal axis of the body lumen. Image generator board 74 is also coupled to a real-time image display 82, which displays the real-time video and can also display the mosaic image created from the video imaging of the body lumen of a patient using the technique described herein.

TABLE 1

| Attribute | Value | Comment |
| --- | --- | --- |
| Capsule shape | 6.35 mm diameter, 18 mm long | standard No. 2 capsule |
| Capsule weight | 0.6 grams | housing made of polyphenylene oxide |
| Fiber scanner | 4.3 mm cantilever of 125 micron diameter | single mode optical fiber |
| Resonant scanning | 5 KHz | amplitude modulated drive |
| Spiral scan | 250 ring spiral per frame | amplitude modulated sine wave and cosine waves |
| Frame rate | 15 Hz | 30 Hz in development |
| Objective lenses | 2.0 mm diameter | window for imaging in air and liquid |
| Forward view | 100 to 120 degrees maximum field of view | able to image in air and water |
| Image resolution | 500 pixels across image | spatial resolution of <100 microns |
| Depth of focus | at least 45 mm axially | able to image side walls of esophagus |
| Tether diameter | less than 1.5 mm | smooth, soft, and supple for swallowing |

During operation, the RGB light from optical fiber combiner 58 is coupled into the core of the singlemode optical fiber that is used to supply illumination light to the TCE. Piezoelectric tube 40 (see FIG. 3) is driven with an amplitude-modulated sine wave supplied to energize selected conductive quadrants formed on the piezoelectric tube. The frequency of the amplitude-modulated sine wave is tuned to approximately equal the scanning fiber's first mode of mechanical resonance (currently, about 5 KHz, for this exemplary embodiment). Light emitted from the end of the singlemode scanning optical fiber passes through lens system 42 and is focused onto the tissue. Light reflected from the tissue is collected by multimode optical fibers 24, routed through color separation system 68 (FIG. 4), and detected by the PMT optical detectors.

Scan generator board 62 and image generator board 74 are custom hardware boards, and each include specific FPGAs and five memory banks. The logic in these FPGAs generates and processes signals to construct the final TCE images or video. In addition to standard RGB imaging, several different alternative imaging modes have been demonstrated with this technology, including: florescence (for imaging fluorescent light emitted by specific types of tissue and other sources), polarization contrast (for imaging light that is polarized by tissue in a specific manner), and sequential color.

Overview of TCE System and its Operation

The TCE system is operated by coupling the desired TCE probe into the base station comprising a personal computer (PC) (not shown in FIG. 4—see FIG. 14, which is described below). Plugged into a system bus of the PC are two custom peripheral component interconnect (PCI) electronic cards. The scan generator board and the image generator board are thus PCI bus cards that each contain eight analog-to-digital (A/D) converters, eight digital-to-analog (D/A) converters, five banks of parallel accessible static random access memory (SRAM) chips, and a 2-million gate FPGA (e.g., a Spartan 3™, which available from Xilinx). The cards are identical except for the programming provided within the FPGA. One card drives the resonant scanner and is used during system calibration. The second card controls the laser power, constructs images from the PMT detector data signals, and drives real-time image display 82. Control of the TCE system in this exemplary embodiment is implemented using a LabVIEW™ software interface (version 8.01 from National Instruments, Inc.) running on the PC.

In this exemplary embodiment, after opening the control program, the user enters the serial number of the TCE probe being used. The serial number identifies files stored in computer memory that contain data relating to the operation of that specific probe, such as the probe type, its resonant frequency, and drive parameters that can be applied to achieve a desired scan pattern and field-of-view for the application. Once the TCE probe parameters are loaded, the TCE probe enters an imaging mode and can be used for imaging inside a lumen disposed within a patient's body.

During imaging, the TCE user interface enables a user to capture and store single image frames or a sequence of frames comprising a video or movie. The captured video can be used by novel mosaicing software (as described below) to create a panoramic image of the esophagus or other internal body lumen. Additional controls enable selective image zooming (performed by driving the resonant fiber to image with a smaller field-of-view) and laser power control. If the user desires to change performance parameters, the device can be recalibrated or again white balanced by coupling the probe to specific calibration or white balance ports, respectively, and selecting the desired function from the user interface.

Tethered Capsule Endoscope Testing

In vitro testing was done to confirm image color balance using color charts (in this exemplary test, a Gretag MacBeth Mini Color Checker chart was used, available, for example, from Edmund Optics), and FOV and resolution were checked using a USAF 1951 photo paper resolution test target (also available from Edmund Optics) in both air and water. An electrical safety test was also conducted and confirmed in vitro. The safety testing protocol included the steps of turning on the TCE instrument, immersing the capsule and the tether in a 200 ml glass beaker filled with physiological buffered saline (over-the-counter NeilMed Sinus Rinse, 8 oz or 235 ml) and placing a stainless steel conducting electrode at least 1 cm away from the probe. Imaging of test targets placed under the beaker commenced while current from the electrode to ground was measured using a precision multi-meter (e.g., a Tenma, Model 72-2050™). No leakage current was detected at the detector's 200 nanoamp noise limit. Detection of any measurable leakage current above the noise floor of 0.2 microamps would cause any in vivo testing to be canceled.

In vivo testing using a porcine model was conducted at the University of Washington, in accordance with approved protocols for animal welfare. A young pig (weighing about 20 kg) was fasted for 8 hours, anesthetized, intubated, and placed on artificial ventilation while placed in the supine position. The esophagus-stomach junction was initially observed and measured using a forward viewing flexible bronchoscope (i.e., a PENTAX, Model EB-1970K™), and large amounts of bile were observed. A suction tube was inserted down the esophagus of the pig to remove most of the bile before inserting the TCE probe. Since the animal was anesthetized and could not be induced to swallow, a capsule introducer was devised and included a flexible tube with a side slit and a custom plastic saddle at the distal tip for holding the TCE capsule. After insertion into the pig's stomach (verified by imaging), a wire was used to push forward and release the TCE capsule from the saddle. The insertion tube was withdrawn about 10 cm leaving the TCE probe within the upper stomach. Together, the TCE tether and insertion tube were slowly pulled out of the pig's esophagus, while TCE video images were recorded at the base station.

A second TCE probe was fabricated and tested for leakage current, cleaned and sterilized with alcohol, and swallowed by a human volunteer in a sitting position. After the volunteer swallowed a few sips of water, the TCE entered the stomach and was slowly pulled back into the upper esophagus while recording video images. In total, the testing took about ten minutes for several iterations of swallowing and removal of the TCE, in this manner.

Overview of Mosaic Software Design and Theory

To create a representation of the esophageal surface using an endoscopy video sequence, two basic elements are required: (1) a surface model of the esophagus; and, (2) a camera pose estimation for each video frame. (In this discussion, the term "camera" is used to represent the function performed by the scanning fiber in the exemplary embodiment of the TCE discussed above, i.e., to form images of a generally cylindrical surface, but it should be understood that the present approach described herein for creating a representation of a generally cylindrical body lumen surface is not limited to any specific type of imaging device. Indeed, other types of imaging devices, including a conventional endoscope, can be employed for producing the image of the interior surface of a generally cylindrical body lumen, such as the esophagus.) With the knowledge provided by these two elements noted above, it is possible to project each frame onto the model to texture-map its surface. The texture-mapped model must then be transformed into a flat image. The internal surface of the esophagus can be modeled as a cylinder, because the esophagus generally has the shape of a cylinder and because a cylinder can be easily displayed as a two-dimensional (2-D) image, if "unrolled."

Pose estimation is done by defining a warping function between neighboring video frames. This warping function is based on an inverse projection of one image onto the mosaicing surface followed by a projection onto another image plane. The warp is a function of the pose parameters of both images and the surface parameters and is used to define an intensity minimization between frames, using the framework of Lucas-Kanade alignment. Each image is compared to at least its two neighbors in the sequence, but this technique results in two (likely inconsistent) pose estimations for each frame. The series of duplicate pose estimations are not readily combined into a single camera path, so the registration is done as a global minimization across all frames.

From each projected frame, a strip having a width corresponding to the amount of forward motion is extracted. These strips, concatenated together, constitute the texture mapped cylinder. When unwrapped, the texture mapped cylinder becomes the mosaic panoramic image. As a final step to compensate for any seaming artifacts, gradient domain blending is used. FIG. 11A shows an exemplary esophageal mosaic image without gradient blending applied, and FIG. 11B shows the mosaic image with gradient blending, to illustrate the benefit of performing this blending step.

This mosaicing technique is most closely related to a prior art technique developed by Rousso et al., who introduced the idea of a pipe projection that allows the mosaicing of video containing forward motion. The pipe projection transforms radial optical flow into parallel optical flow lines, enabling projected images to be stitched via a simple shift. However, the viewing pipe in this earlier approach does not necessarily correspond to the physical lumen in a patient's body. The viewing pipe in Rousso et al. is defined by placing the camera's optical center and the focus of expansion on the pipe's central axis, which would certainly not be the case for an entire video sequence of a physical lumen. Indeed, the pipe mosaicing algorithm might produce a mosaic where the input images are stitched together seamlessly, but it would likely significantly distort the interior surface of the lumen in the resulting mosaic image. If a camera is moved straight down a lumen, but is off center, for example, the side closer to the camera will be magnified relative to the other side. Pipe projection enables sequences exhibiting forward motion to be mosaiced by transforming radial optical flow into parallel optical flow in the projected image. Instead, the mosaicing approach that is used should enable mosaicing on the surface of the physical lumen, and not use a pipe as a manifold to transform optical flow.

The input to the algorithm used for the present exemplary approach is a set of perspective views from a camera moving within a known type of surface, such as a cylinder. From this sequence, the 6 degrees-of-freedom (DOF) camera pose for each frame is estimated, and optionally, parameters describing the surface shape are estimated, if they are not fully known. For a known pose, each frame is projected onto the surface, which can be displayed as a flat image constituting the mosaic image. Pose estimation is done by defining a warping function between successive video frames. This warp is based on the step of projecting one frame onto the mosaicing surface and taking a virtual view from the location of the template frame; it is a function of the pose parameters of both frames and the surface parameters. This warp is used to define an intensity minimization between frames, which is a well studied problem. The Lucas-Kanade algorithm is used to solve for the warp between two frames, giving the pose of each. To compute a consistent set of warps across all frames, the process solves for all of the warps between successive frames globally; the computation of a consistent pose estimate for each frame tends to be much more stable than pair wise estimates. Once the camera poses are known, generating the mosaic is just a problem of selecting the appropriate patches from each frame so as to get the best resolution and produce a seamless composite mosaic image.

Exemplary Embodiment of Surface Projection Warp

The image warp to be solved for is modeled as a combination of a perspective projection from one camera location onto a mosaic surface, followed by an inverse projection to another camera location. An arbitrary surface S in three-dimensional space can be parameterized by two variables, a=(a, b). Since the registration technique used in this exemplary embodiment is based on warping one video frame to another, it is necessary to convert from image coordinates to surface coordinates and vice-versa to do a complete warp. Alternatively, the optimization could be formulated to compare forward projections of two images, but the frame-to-frame warping employed in this embodiment has the advantage that one image remains static and also provides a more straightforward method to work on a single input pixel resolution.

The relationship between the 3-D surface point S(a) and its two-dimensional (2-D) image coordinates u=(u, v, f) can be described by:

$$S = x + R_{xyz} uc$$

where x=(x, y, z) is the position of the camera, $R_{xyz}=R_x(\alpha)R_y(\beta)R_z(\gamma)$ is the rotation matrix representing the camera's orientation, and c is the scale factor required to intersect the projective surface. The quantity $R_{xyz}u$ is the direction from the optical center to the 3-D pixel location, adjusted to the coordinate system of the surface.

Depending on the type of surface involved, it is possible to solve for the surface variables (a, b) and the scale factor c, giving the projective warp $$\begin{bmatrix} a \\ b \end{bmatrix} = P\left(\begin{bmatrix} u \\ v \end{bmatrix}, X\right)$$

where $X=(x,y,z,\alpha,\beta,\gamma)$ contains the six-degree-of-freedom camera pose. The warp is defined such that the intersection with the smallest positive c is used if there are multiple ray-surface intersections.

The inverse projective warp is simpler to solve for since it doesn't depend on knowing the function S. It is only necessary to find the point in the image plane corresponding to the scene point using the surface function. From the equation $$u = R_{xyz}^{-1}(S-x)/c$$

it is possible to easily find c and thus, achieve the inverse projection $$\begin{bmatrix} u \\ v \end{bmatrix} = P^{-1}\left(\begin{bmatrix} a \\ b \end{bmatrix}, X\right).$$

An image can now be projected onto the surface from one pose and a virtual view can be made from another pose. Composing the projection and inverse projection, one frame can be warped to another by defining the warping function:

$$W(u,X_1,X_2) = P^{-1}(P(u,X_1),X_2).$$

The case of a cylindrical surface is derived by letting a=θ be the surface points angular distance around the cylinder and b=k be its depth. Then $$S(a, b) = \begin{bmatrix} r\cos(\theta) \\ r\sin(\theta) \\ k \end{bmatrix}$$

and the relation between surface coordinate and image coordinate becomes $$\begin{bmatrix} r\cos(\alpha) \\ r\sin(\alpha) \\ k \end{bmatrix} = \begin{bmatrix} x \\ y \\ z \end{bmatrix} + R \begin{bmatrix} u \\ v \\ f \end{bmatrix} c.$$

If u and v are known, it is possible to solve for c by noting:

$$r^2 = (r\cos(\alpha))^2 + (r\sin(\alpha))^2 = (c(Ru)_x + x)^2 + (c(Ru)_y + y)^2.$$

This result produces a quadratic in c. With a known c, it follows that $$\alpha = \arctan((y + P_y c)/(x + P_x c)) \text{ and } k = z + (Ru)_z c.$$

Pair Wise Pose Estimation

Given the warp defined in the previous section, it is desired to solve for a warp that minimizes the sum squared difference between two frames. That is, it is desirable to find $X_1$ and $X_2$ that minimize the error, E, as defined by the function:

$$E = \sum_{pixels\ u} [I_1(u) - I_2(W(u, X_1, X_2))]^2.$$

A Lucas-Kanade style forwards additive approach is employed to achieve this result, as is known in the art. The forwards additive algorithm is computationally more expensive than the alternatives, but since the set of warps does not generally form a semi-group or group, the other compositional algorithms aren't applicable. Furthermore, the requirements for inverse additive approach are not satisfied. Given a current estimate of $X_1$ and $X_2$, the goal is to find iterative updates $\Delta X_1$ and $\Delta X_2$ that reduce the error function $$\sum_{pixels\ u} [I_1(u) - I_2(W(u, X_1 + \Delta X_1, X_2 + \Delta X_2))]^2.$$

The closed form additive update for this equation is $$\begin{bmatrix} \Delta X_1 \\ \Delta X_2 \end{bmatrix} = H^{-1} b$$

where H is the Hessian $$H = \sum_u \left[ \nabla I_2 \frac{\partial W}{\partial (X_1, X_2)} \right]^T \left[ \nabla I_2 \frac{\partial W}{\partial (X_1, X_2)} \right],$$

and b is the residual $$b = \sum_u \left[ \nabla I_2 \frac{\partial W}{\partial (X_1, X_2)} \right] [I_1(u) - I_2(W(u, X_1, X_2))].$$

The warping function is the combination of two projections, so the Jacobian of the warp can be expressed in terms of the Jacobians of the projections $$\frac{\partial W}{\partial (X_1, X_2)} = \left[ \frac{\partial P^{-1}}{\partial a} \frac{\partial P}{\partial X_1} \quad \frac{\partial P^{-1}}{\partial X_2} \right].$$

In order to compute the Jacobian, it is necessary that the surface function be differentiable. Depending on the surface type, deriving the Jacobian can become quite a long process, although not necessarily complex.

The pose parameters are initialized based on the generally cylindrical surface of a body lumen, and the camera is expected to be oriented axially, facing directly down the lumen. All frames are given the same initial pose. For convenience, the world coordinates should be chosen so that the default pose corresponds to the zero vector X=0. There can be ambiguities in the warp for a circular cylinder, which is radially symmetric. In these cases it may be desirable to partially constrain one of the frames. The iterative update can be run on a coarse-to-fine basis to handle motion greater than one pixel and for computational improvement. When transitioning from a coarser to a finer iteration, the positional pose parameters need to be scaled along with the surface, but the orientation parameters should not be.

Global Pose Estimation

The algorithm outlined above will estimate the pose of two images, but when dealing with an entire video sequence, the pose of every frame is of interest. A common approach is to align pairs of frames sequentially, but this does not work in this case because the warping parameters are not independent. A sequential registration would likely produce two different pose estimates for each frame, one from the warp to the previous frame, and one from the warp to the next. To obtain a consistent set of pose estimations, the pair wise optimizations are reformulated into one global optimization that minimizes the error between successive frames simultaneously.

The error function that is to be minimized is a sum of the pair wise error, $$E = \sum_{i=1}^{n-1} \sum_{pixels\ u} (I_i(u) - I_{i+1}(W(u, X_i, X_{i+1})))^2.$$

The process continues with deriving the Jacobian for the warp between frame i and i+1, $$J_i = \frac{\partial W(u, X_i, X_{i+1})}{\partial (X_1, X_2, \ldots, X_n)},$$

the Hessian $$H = \sum_{i=1}^{n-1} \sum_u [\nabla I_{i+1} J_i]^T [\nabla I_{i+1} J_i],$$

and the residual, $$b = \sum_{i=1}^{n-1} \sum_{u} [\nabla I_{i+1} J_i][I_i(u) - I_{i+1}(W(u, X_i, X_{i+1}))].$$

The iterative update becomes $$\begin{bmatrix} \Delta X_1 \\ \vdots \\ \Delta X_n \end{bmatrix} = H^{-1}b.$$

Note that for any particular warp, the Jacobian is mostly empty, only containing nonzero entries for only the pose parameters affecting that warp. The Hessian for the global optimization is a 6n×6n square matrix. However, since only consecutive frames are compared, the Hessian is sparse and banded, enabling this problem to be solved efficiently. The global Hessian and residual can be constructed from their pair wise counterparts, as is illustrated in FIG. 13C. As indicated in this Figure, the banded Hessian matrix is constructed from Hessians of the pair wise registration, and overlapping regions are summed.

A global optimization has been demonstrated above, where each frame is compared to the immediately previous and next frames. However, this method is easily extended to compare each frame to any number of neighbors, at the cost of computational complexity.

Shape Adjustment

The discussion above concentrated on solving for camera pose, assuming the surface is known. However, if the surface is known to be within a parameterized family, it is a simple extension to add variables controlling the surface shape into the optimization. If s describes the shape of the surface, then the surface projections function becomes $$W(u, X_1, X_2, s) = P^{-1}(P(u, X_1, s), X_2, s).$$

The surface parameters are treated just like the pose parameters, resulting in the Jacobian for the warp between frame i and i+1.

$$J_i = \frac{\partial W(u, X_i, X_{i+1}, s)}{\partial (X_1, X_2, \ldots, X_n, s)}$$

The iterative update scheme becomes $$\begin{bmatrix} \Delta X_1 \\ \vdots \\ \Delta X_n \\ \Delta s \end{bmatrix} = H^{-1}b,$$

where the Hessian and residual are defined just as before. Examples of this extension include an elliptical cylinder with unknown relative semi-major and semi-minor axes, or any other surface that varies by being stretched in one dimension.

Additional Information

Information obtained from sources besides optical flow can be incorporated into the registration algorithm to improve performance. Pixels can be weighted or ignored based on a quality measure, such as the camera's signal-to-noise ratio. This step can be done independently in each color channel, providing better registration if a particular color channel is noisy. Additionally, the algorithm can ignore entire video frames if they are deemed to be of poor quality. These alterations can be done as a preprocessing step, or can be carried out in real time as the program runs.

If the camera is generally known to follow a stable trajectory, this information can also be used to constrain the registration. The general formulation of the registration algorithm enables the pose parameters of neighboring frames to be arbitrarily different. Since the video or sequence of images is known to be taken from a tethered camera, the motion can be assumed to be much less chaotic. The iterative updates can be weighted to give preference to a family of know trajectories, yielding a stability and performance improvement.

Pipe Projection and Strip Selection

With a known relative pose of a video frame and the surface, it is possible to relate image coordinates and mosaic coordinates using a perspective projection on an image plane 104. The position of the camera within a body lumen can be determined by monitoring the tether as the camera is pulled through the body lumen, as the video sequence is being captured. The mosaiced image that is produced can be thus be scaled to the body lumen, enabling medical personnel to determine specific positions in the body lumen, e.g., where diseased conditions of the tissue are evident in the mosaiced image. An automatic monitor, such as camera position monitor 19 (FIG. 4) can be provided to track the movement of the tether and thus the position of the camera within the body lumen, as the camera is moved through the body lumen to capture the video sequence.

Strips 106 used to make the mosaic are determined by a "scanning broom." An exemplary internal surface image 110 is shown in FIG. 6A. Any line 112 selected in the video frame will "sweep" over the scene (thus, the term "scanning broom") as the video is played (see FIG. 6B). The shape of this scanning broom depends on the motion in the scene, ideally being perpendicular to the optical flow. In the case of forward motion, the shape is an ellipse centered around the focus of expansion. Strips 114 (an example of one strip is shown in FIG. 6C) are defined implicitly based on knowledge of a camera position (depth in the pipe) for each frame or image. An elliptical scan line in the frame is defined implicitly by selecting a distance down the pipe from a given frame's center of projection. After determining the change in depth for a particular frame, this value is added to the chosen distance to define another line in the frame. The area between these two lines is the strip to be added to the mosaic. Occasionally, the elliptical strip will stray outside of the frame boundaries, which is addressed by simply leaving the corresponding areas of the mosaic to be filled in by subsequent frames. These areas are guaranteed to come into view, because the camera is moving backward. As a result, the sampling strip appears to hug the edge of the frame when the strip would otherwise extend out of frame.

Neighborhood Normalization and Blending

The alignment method that is used relies on a few assumptions, notably, constant lighting, small motions, and smooth gradients. The small-motion issue is addressed with courseto-fine alignment and the smoothness problem can easily be fixed by blurring the images. Constant illumination is an issue because the light source is on the camera itself in this exemplary embodiment, so lighting changes as the camera moves. This issue is addressed using neighborhood normalization. In neighborhood normalization, the mean intensity and standard deviation are computed for a small window around each pixel. By subtracting the mean from the pixel value and dividing by the standard deviation, some measure of a point's actual color independent of the lighting conditions is obtained. The resulting image can then be used for the pair wise alignment, satisfying the color-constancy assumption. FIG. 10A illustrates an exemplary original image of an esophagus, while FIG. 10B illustrates a neighborhood-normalized frame, where both images were derived from endoscopy video. Neighborhood normalization allows compensation for illumination differences between frames.

Imperfect alignment and changing illumination result in noticeable seams along the strip boundaries. It is preferable to minimize these seams without removing any details from the image. A simple blending approach, like feathering, usually requires a large overlap with good registration to avoid ghosting, but in the present case, the registration is only likely to be good in a small region along the seam. Instead, gradient domain blending is used.

Rather than accumulating strips of pixel color values, the color gradients are accumulated. The gradients themselves can be blended with feathering over a small area. The result is a gradient vector field for each color channel. It is then possible to solve for an image that has the associated gradient field. Since there are two equations per pixel, it is an over-constrained problem, and a best-fit solution must be found. Each pixel gives two equations of the form: $I(x+1,y)-I(x,y)=I_x(x,y)$ and $I(x,y+1)-I(x,y)=I_y(x,y)$ per color channel, where $I_x$ and $I_y$ are known. Arranging I into a large vector v, and $\nabla I$ into a vector w gives the matrix equation:

$$Mv=w,$$

where M is a sparse matrix containing two rows for each pixel (minus the boundary cases). A least-squares fit can be found by multiplying both sides by $M^T$. The matrix $M^TM$ gives the Laplacian of an image when represented in vector form, so in essence, the image is derived from its associated Laplacian.

Results

The completed TCE system (base station and probe) meet all design criteria listed in Table 1 and this system is shown in FIGS. 2A, 2B (TCE probe and tether), and 7A (which illustrates the full system). During TCE operation, the measured total laser power at maximum power setting is about 1.5 mW (B-442 nm), 2.3 mW (G-532 nm), and 3.6 mW (R-635 nm) for the color components, as measured using an optical power meter and probe (Newport 1830-C™ and 818-ST™). In comparison to standard video endoscopes and bronchoscopes, the maximum TCE optical power is 3× less than mid-range illumination, and 40× less than full-power illumination when measurements are made at a 532 nm responsivity of the silicon sensor. In vitro imaging of flat test targets (e.g., the Gretag Macbeth Mini Color Chart shown in FIG. 7C and Edmund Optics USAF 1951 test target shown in FIG. 7B) demonstrates the high color saturation and spatial resolution. Target number 3-3 has a 49.0 micron bar width which can be resolved in the peripheral field of FIG. 7B. The TCE probe for animal testing measured just over 100 degrees FOV, while the TCE probe for human testing measured just below 100°. When placed within a 1-inch tube of rolled paper on which was imprinted a map of the area around Japan and pulled slowly (~2 mm/sec), while remaining roughly centered in the central axis of the lumen, mosaic images are generated with noticeable, but acceptable, levels of distortion for the purpose of identifying and mapping regions of color variation (as shown in FIG. 7D). The TCE system images appear similar in both air and water mediums, and no measurable leakage current was detected while imaging in physiological buffer.

Another exemplary mosaic shown in FIG. 12D was created for a world map image. The paper on which the world map was imprinted was rolled to form a 10 inch diameter, 5 ft. long tube lined with the rolled world map, which is shown in FIG. 12A before being formed into the cylindrical tube. The camera was inserted into the tube on a plastic tray (not separately shown). The video was taken with a consumer camcorder (not separately shown—as an example that employs a different type of camera than the exemplary TCE described herein). The scene was unevenly lit, as is apparent in the exemplary input video image frames shown in FIGS. 12B and 12C. Along with a limited depth of field, these issues made the registration challenging. The resulting mosaic shown in FIG. 12D is constructed from strips taken from 400 such video frame images. The bottom of the map is cut off in this mosaic image, since the bottom of the world map was not visible on the inner surface of the map after being rolled to form the cylindrical tube. The mixed exposure evident in the mosaic image of FIG. 12D was caused by uneven lighting conditions within the cylindrical tube. Despite the low quality input video, the mosaic image produced using the 6 DOF algorithm closely matches the reference image of FIG. 12A, demonstrating the algorithm's capability for metric accuracy.

TCE testing within the live pig revealed images of the lower esophagus to mouth with a mosaic image of the upper esophagus, shown in FIG. 8A, which was produced from images of the upper esophagus shown in FIG. 8B. Bright yellow-green bile was present in the pig stomach and particles 120 of bile-coated food appeared on the esophagus walls during imaging of the pig in the supine position. Suction applied to a secondary tube alongside the TCE removed much of the obscuring bile. In a sitting position, the human volunteer easily swallowed the TCE probe using only sips of water and taking several swallows. The TCE probe revealed a clear image of the gastric folds as shown in FIG. 9A, and the important squamo-columnar junction where the stomach mucosa (red) transitions to the esophageal mucosa (light pink) (see FIG. 9B). An image of the mid-esophagus region is shown in FIG. 9C. In human in vivo images, the red TCE illumination was reduced from the maximum in order to match the expected hues per the recommendations of two observing gastroenterologists. To compensate for darker imaging in vivo versus in vitro, TCE images shown in FIGS. 9A, 9B, and 9C were increased in brightness and contrast by 10-20% using photo enhancement software. Occasionally bubbles obscured the esophagus walls. The bubbles were removed from the FOV by draining the residual water, by swallowing, or by adding additional water.

Flowchart Illustrating Exemplary Logic to Produce Mosaic Image

A flowchart 300 in FIG. 13A illustrates the steps of exemplary logic that are used to produce a mosaic image of an internal surface of a body lumen in accord with the present technique. Details of each of these steps are otherwise discussed herein. A step 302 provides for solving for six degrees-of-freedom camera pose parameters p for a video sequence produced by the camera use in the TCE probe. These parameters are determined by iterative minimization so as to minimize an error function, which is itself, a function of the 2-D images produced by the camera, a projection on the scene geometry, and an inverse projection. Details of the iterative steps follow. A step 304 computes local Hessian, $A_1$-$A_{n-1}$ and the residual for consecutive video frames (or images), e.g., as shown in FIG. 8B. In a step 306, each 12×12 matrix $A_i$ is added to the submatrix A[6i−5, . . . , 6i+6; 6i−5, . . . , 6i+6]. Next, in a step 308, each 12−1 matrix $B_i$ is added to the submatrix A[6i−5, . . . , 6i+6; 1]. A step 310 then solves for $\Delta p = A^{-1}(-b)$, and a step 312 updates p. A decision step 314 then determines if p changed and if so, the logic repeats, starting with step 304. Otherwise, the logic continues with a step 316 (FIG. 13B), in which each image $I_i$ is warped with a defined function $W^{-1}(W(x;p_{i+1});p_i)$, to compute $I_i(W^{-1}(X;p_{i-1});p_i))$. Next, error images are computed in a step 318, and a step 320 computes the Jacobian of the warping function. A step 322 computes the image gradient, and a step 324 evaluates the Jacobian of the image warp. In a step 326, the Hessian is evaluated, and a step 328 evaluates the residual, $b_i$.

Discussion

TCE swallowability and imaging performance met all expectations in this first-generation prototype. In one motivated volunteer, the capsule was easily swallowed with no side effects. However, a capsule weighing approximately 150% more may aid in more rapid peristaltic movement into the stomach. It is contemplated that simethicone can be used to reduce bubbles. Because most of the capsule is empty space, adding weight is a minor modification. When recording video for the mosaicing feature, the normal 15 Hz viewing frame rate was reduced to less than 5 Hz. Nonetheless, the mosaic algorithm successfully captures the esophageal surface. Most of the seaming artifacts occur when the camera changes direction or pauses for an extended period of time, but are undetectable after gradient domain blending. Lighting inconsistencies in the input image cause artifacts in the mosaic, which are especially noticeable when the sampling strip covers a specular reflection. Color consistency within the mosaic should improve as the automatic gain control is made more sophisticated, for example, by using gamma correction.

The TCE prototype has one major difference from conventional all camera-based capsule endoscopes, specifically, the versatility of adding advanced imaging features and laser diagnostics while not affecting the size or cost of the TCE probe. By electronically adjusting the scan amplitude, magnification endoscopy can be added as a feature. By selecting individual laser illuminations, narrow band imaging within the visible spectrum can be displayed concurrently with combined RGB imaging. Because each laser reflectance map is generated individually, a post-processing algorithm can be used to enhance color differences within the mosaic image beyond the visible spectrum, using light sources across the ultraviolet to infrared spectrum. By turning off specific laser illuminations and filtering out the higher incident illumination, fluorescence imaging (i.e., to produce images responsive to fluorescent light from tissue) can be employed as an additional feature. Recently, the combination of two advanced imaging techniques, auto-fluorescence and narrow-band, combined with reflectance imaging of BE, has been demonstrated to improve the sensitivity and specificity of detecting neoplasia compared to standard endoscopy. However, there is a risk of information overload with the implementation of multimodal endoscopic imaging in the clinic, possibly opening the door to doctor assistance from computer-aided pattern recognition and diagnosis.

The clinical value and specific role of the TCE image mosaicing feature has yet to be determined. Possible uses are to provide: (1) a color printout of the endoscopy for patient-doctor counseling; (2) a scaled mapping of the regions of BE to more rapidly assist in determining between long segments, short segments, and tongues of BE; (3) a single fused image that combines the results from multiple TCE mosaics from multiple swallowings to reduce ambiguity from a single imaging pass; (4) the ability to map regions of non-visible multimodal image data overlaid in pseudo-color and possibly select biopsy sites; (5) the ability to add quantitative optical biopsy measures based on laser-induced fluorescence and spectroscopy; and, (6) a visual record of the patient's medical history, which also combines multiple sensor data such as pH and sphincter pressure. Currently the mosaic image is generated with less than 5 minutes of post processing of the TCE images, while real-time mosaicing is expected by using graphic processor chips in the future. To accurately scale the mosaic image to esophageal position, a tether position sensor is needed, as previously developed for the BE colorimetry probe. There is a growing need for disease screening programs in developing countries that rely on computer-aided diagnosis with low-cost imaging scopes using easy to follow clinical procedures on unsedated patients.

Exemplary Computing System for Implementing Mosaicing Technique

FIG. 14 illustrates an exemplary computing system 1100 that is suitable for use as a computing device employed for implementing the novel approach described above. Computing system 1100 includes a processor 1112 that is coupled in communication with a generally conventional data bus 1114. Also coupled to the data bus are a memory 1116 that includes both random access memory (RAM) and read only memory (ROM). Machine instructions are loaded into memory 1116 from storage on a hard drive 1118 or from other suitable non-volatile memory, such as an optical disk or other optical or magnetic storage media. The storage can also include files that define the images taken by an endoscope camera. The machine instructions in storage, when transferred to memory 1116 and executed by processor 1112, can cause the processor to carry out a plurality of different functions employed to implement the novel approach, as described herein, as well as other functions.

An input/output (I/O) interface 1120 that includes a plurality of different types of ports, such as serial, parallel, universal serial bus, PS/2, and Firewire ports, is coupled to data bus 1114 and is in turn connected to one or more input devices 1124, such as a keyboard, mouse, or other pointing device, enabling a user to interact with the computing system and to provide input and control the operation of the computing system. A display interface 1122 couples a display device 1126 to the data bus, enabling graphic and text information to be displayed for viewing by a user. A camera or imaging system 1132 is coupled to I/O interface 1120 to convey the signal produced by the camera into the computing system. The computing system is also optionally coupled to a network 1130 and/or to the Internet via a network interface 1128, which couples to data bus 1114.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for creating a mosaiced image of an inner surface of a body lumen, comprising the steps of:
   (a) moving an imaging device through the body lumen;
   (b) capturing a video sequence comprising successive images of the inner surface of the body lumen as the imaging device is moved through the body lumen;
   (c) determining pose parameters defining a position and an orientation for the imaging device, when capturing the video sequence of the inner surface of the body lumen, wherein the steps of determining pose parameters includes the steps of defining a warping function that simultaneously minimizes an error between successive images; and warping one image to another image with the warping function;
   (d) based upon the pose parameters, projecting the successive images onto a model of the inner surface, to form a texture-mapped model; and
   (e) transforming the textured mapped model into the mosaiced image that is on a generally flat surface.

2. The method of claim 1, further comprising the step of presenting the mosaiced image to a user.

3. The method of claim 1, wherein the step of determining the pose parameters comprises the step of determining a set of global pose parameters so as to minimize a predefined error function.

4. The method of claim 1, wherein the step of defining a warping function that simultaneously minimizes the error between successive images comprises the steps of:
   (a) defining an error between one image and a warp of a successive image determined with an estimated warping function;
   (b) deriving a Jacobian for the estimated warping function between the one image and at least one successive image, a corresponding Hessian, and a residual;
   (c) updating the estimated warping function to produce a new warping function; and
   (d) iterating preceding steps (a)-(c) until the error in step (a) is minimized, the warping function that simultaneously minimizes the error between successive images being a then current estimated warping function.

5. The method of claim 1, wherein the step of defining the warping function that simultaneously minimizes the error between successive images comprises the step of including a shape adjustment corresponding to at least an approximate shape of the model of the inner surface in the warping function.

6. The method of claim 1, further comprising the step of determining a position of the imaging device within the body lumen while capturing the video sequence, to enable scaling the mosaiced image in relationship to the body lumen.

7. The method of claim 1, further comprising the step of applying a normalization to the mosaiced image to minimize an effect of lighting differences between successive images.

8. The method of claim 7, wherein the step of applying a normalization comprises the step of using neighborhood normalization around pixels comprising the mosaiced image.

9. The method of claim 1, further comprising the step of applying gradient domain blending to the mosaiced image to minimize banding between successive images where adjacent edges of the successive images are projected to form the mosaiced image.

10. The method of claim 1, further comprising the step of reducing color inconsistencies in the mosaiced image by employing an automatic gain control during the step of capturing the video sequence.

11. The method of claim 1, further comprising the step applying post-processing to enhance color differences within the mosaiced image for light that is outside a visible spectrum, to enable characteristics of the inner surface of the body lumen that are not as evident in the visible spectrum, to be better seen.

12. A memory medium on which machine readable and executable instructions are stored, for carrying out the steps (c)-(e) of claim 1.

13. A system for creating a mosaiced image of an inner surface of a body lumen, comprising:
   (a) an imaging device configured and sized to be inserted into a body lumen for producing an output signal corresponding to images of an inner surface of a body lumen as the imaging device is moved there through;
   (b) a memory in which a plurality of machine instructions are stored;
   (c) a display on which graphic images can be presented to a user;
   (d) a processor coupled to the display and the memory, the processor executing the machine instructions stored in the memory to carry out a plurality of functions, including:
      (i) capturing a video sequence comprising successive images of the inner surface of the body lumen as the imaging device is moved through the body lumen;
      (ii) determining pose parameters defining a position and an orientation for the imaging device, when capturing the video sequence of the inner surface of the body lumen, wherein the pose parameters are determined by defining a warping function that simultaneously minimizes an error between successive images; and warping one image to another image with the warping function;
      (iii) based upon the pose parameters, projecting the successive images onto a model of the inner surface, to form a texture-mapped model; and
      (iv) transforming the textured mapped model into the mosaiced image that is on a generally flat surface.

14. The system of claim 13, wherein the machine instructions further cause the processor to present the mosaiced image to a user.

15. The system of claim 13, further comprising a tether that is coupled to the imaging device and is usable for moving the imaging device through a body lumen and for conveying the output signal from the imaging device.

16. The system of claim 13, wherein the machine instructions further cause the processor to determine a set of global pose parameters that minimize a predefined error function.

17. The system of claim 16, wherein the machine instructions further cause the processor to include a shape adjustment corresponding to at least an approximate shape of the model of the inner surface when defining the warping function.

18. The system of claim 13, wherein to define a warping function that simultaneously minimizes the error between successive images, the machine instructions cause the processor to:
   (a) define an error between one image and a warp of a successive image determined with an estimated warping function;
   (b) derive a Jacobian for the estimated warping function between the one image and at least one successive image, a corresponding Hessian, and a residual;
   (c) update the estimated warping function to produce a new warping function; and
   (d) iterate preceding functions (a)-(c) until the error is minimized, the warping function that simultaneously minimizes the error between successive images being a then current estimated warping function.

19. The system of claim 13, further comprising means for monitoring a position of the imaging device within a body lumen, wherein the machine instructions further cause the processor to employ said means to determine the position of the imaging device within the body lumen while capturing the video sequence, and to scale the mosaiced image in relationship to the body lumen.

20. The system of claim 13, wherein the machine instructions further cause the processor to apply a normalization to the mosaiced image to minimize an effect of lighting differences between successive images.

21. The system of claim 20, wherein the normalization that is applied is a neighborhood normalization around pixels comprising the mosaiced image.

22. The system of claim 13, wherein the machine instructions further cause the processor to apply gradient domain blending to the mosaiced image to minimize banding between successive images, where adjacent edges of the successive images are projected to form the mosaiced image.

23. The system of claim 13, wherein the machine instructions further cause the processor to reduce color inconsistencies in the mosaiced image by employing an automatic gain control when capturing the video sequence.

24. The system of claim 13, wherein the machine instructions further cause the processor to enhance color differences within the mosaiced image for light that is outside a visible spectrum, to enable characteristics of an inner surface of a body lumen that are not as evident in the visible spectrum, to be better seen.

25. The system of claim 13, wherein the imaging device includes a scanning optical fiber that is driven to move in a desired scanning pattern to image an inner surface of a body lumen in which the imaging device is inserted.

26. The system of claim 25, further comprising an optical fiber for conveying illumination light from a source to the scanning optical fiber.

27. The system of claim 25, further comprising at least one optical fiber for conveying the output signal from the imaging device, so that the output signal can be detected externally of a body lumen.

* * * * *